United States Patent [19]

Shen et al.

[11] Patent Number: 5,683,695

[45] Date of Patent: Nov. 4, 1997

[54] PRODUCTION OF RECOMBINANT PROTEINS CONTAINING MULTIPLE ANTIGENIC DETERMINANTS LINKED BY FLEXIBLE HINGE DOMAINS

[75] Inventors: De Fen Shen, Kew Garden Hill; Chang Yi Wang, Cold Spring Harbor, both of N.Y.

[73] Assignee: United Biomedical, Inc., Hauppauge, N.Y.

[21] Appl. No.: 15,770

[22] Filed: Feb. 10, 1993

[51] Int. Cl.$^6$ .......................... A61K 39/00; C07H 21/04; C07K 14/00; C12N 15/00

[52] U.S. Cl. ...................... 424/185.1; 424/192.1; 424/201.1; 424/202.1; 424/203.1; 435/252.3; 435/320.1; 530/324; 530/350; 536/23.1; 536/23.4; 536/23.5; 536/23.53; 536/23.72

[58] Field of Search .................. 424/184.1, 185.1, 424/188.1, 189.1, 192.1, 193.1, 196.11, 197.11, 201.1, 202.1, 203.1; 435/69.1, 69.3, 69.7, 320.1, 240.1, 252.3; 530/350, 329, 324, 391.1, 403–405; 536/23.1, 23.4, 23.5, 23.53, 23.72, 23.74

[56] References Cited

U.S. PATENT DOCUMENTS

| | | | |
|---|---|---|---|
| 4,818,527 | 4/1989 | Thornton et al. | 424/88 |
| 5,013,653 | 5/1991 | Huston et al. | 435/69.7 |
| 5,019,387 | 5/1991 | Haynes et al. | 424/89 |
| 5,023,077 | 6/1991 | Gevas et al. | 424/88 |
| 5,041,533 | 8/1991 | Wunsch et al. | 530/317 |

OTHER PUBLICATIONS

Morode et al. (1988) Peptide Chemistry 1987: T. Shiba and S. Sakakibara (eds) Protein Res. Foundation, Osaka pp. 759–764.
Morder et al. (1990) Tetrahedron 46(9):3305–3314.
Wunscheral (1991) Int. J. Peptide Protein Res. 37:90–102.
Moroder et al. (1991) Biopolymers 31:595–604.
Nardelli et al. (1992) J. Immunology 148:914–920.

Zorzato et al. (1990) J. Biol. Chem. 265:2244–2256.
Corteg et al. (1990) 348:176–178.
McGeoch et al. (1986) Nucleic Acids Res 14:1727–1745.
Krieg et al. (1989) Nucleic Acid Res. 17:10321–10335.
Meyers et al, Eds., (1992) Pub: Theoretical Biology and Biophysics Group T–10 Los Alamos National Laboratories, Los Alamos, New Mexico. "Human Retroviruses and AIDS 1992".
Hunkapillar et al, (1986) *Nature* 323:15–16. "The Growing Immunoglobulin Gene Superfamily".
Williams, (1987) Immunol. Today, 8:298–303. "A Year in the Life of the Immunoglobulin Superfamily".
Haseman et al, (1989) in Fundamental Immunology, Second Edition (Paul, Ed.) Raven Press Ltd., New York, New York, pp. 209–233. "Immunoglobulins: Structure and Function".
Moss, (1991) Science 252:1662–1667. "Vaccina virus: A Tool for Research and Vaccine Development".
Graham, Tibtech, 8:85–87 (1990). "Adenoviruses as expression vectors and recombinant vaccines".
Prevec et al, (1989) J. Gen. Virol. 70:429–434. "Use of Human Adenovirus–based Vectors for Antigen Expression in Animals".

(List continued on next page.)

*Primary Examiner*—Ponnathapura Achutamurthy
*Attorney, Agent, or Firm*—Morgan & Finegan, L.L.P.

[57] ABSTRACT

The present invention relates to recombinant proteins encoding at least two antigenic epitopes joined by flexible hinge domains. Proteins of this design enable presentation of each epitope to the immune system and are particularly useful as vaccines against infectious agents, such as viruses, when many variants of that agent exist. Moreover, the recombinant proteins of the invention are useful as a single vaccine composition effective against diverse infectious agents since the subject proteins can have antigenic epitopes from different infectious agents. The invention further provides nucleic acids, expression vectors, host cells and methods for production of the subject recombinant proteins as well as vaccines and methods for treating HIV.

2 Claims, 8 Drawing Sheets

OTHER PUBLICATIONS

Liang et al, (1992) Virology 189:629–639. "An in Vivo Study of a Glycoprotein gIII–Negative Bovine Herpesvirus 1 (BHV–1) Mutant Expressing Beta–galactosidase: Eval. of Role of gIII in Virus Infectivity & Use as Vector for Mucosal Immunization".

Rovinski et al, (1992) J. Virol. 66:4003–4012. "Expression and Characterization of Genetically Engineered Human Immunodeficiency Virus–Like Particles Containing Modified Envelope Glycoproteins: Implications for Development of a Cross–Protective AIDS Vaccine".

Michel et al, (1988) *Proc. Natl. Acad. Sci.* 85:7957–7961. "Induction of anti–human immunodeficiency virus (HIV) neutralizing antibodies in rabbits immunized with recombinant HIV–hepatitis B surface antigen particles".

Michel et al, (1990) *J. Virol.* 64:2452–2455. "T–and B–Lymphocyte Responses to Human Immunodeficiency Virus (HIV) Type 1 in Macaques Immunized with Hybrid HIV/Hepatitis B Surface Antigen Particles".

FIG. 2

```
                        C   R   I   K   Q   V   I   M   M   W
       GGA TCC GTT AAC GGC TGC AGA ATC AAA CAG GTC ATC AAC ATG TGG
                        A start Q   E   V   G   K   A   M   Y   A   P   P   I   S   G   Q   I
CAG GAA GTT GGT AAA GCT ATG TAC CGT CCG CCG ATC TCT GGT CAG ATC R   C   D   P   P   D   P   D   P   K   A   I   H   I   G   P
CGT1TGT GAT CCG CCA GAT CCG GAT CCG AAA CGT ATC CAC ATC GGT CCG
                                        MN  start G   R   A   F   V   T   T   K   N   P   P   D   P   D   P   R
GGT CGT GCT TTC GTT ACC ACC AAA AAC CCG CCA GAT CCG GAT CCG CGA
    15                       MN  end                             SC S   I   H   I   G   P   G   R   A   F   V   A   T   G   D   P
TCT ATC CAC ATC GGT CCG GGT CGT GCT TTC GTT GCT ACC GGT GAT CCG
                                                         SC end
    20
 P   D   P   D   P   K   S   I   R   I   T   K   G   P   G   R
CCA GAT CCG GAT CCG AAA TCT ATC CGT ATC ACC AAA GGT CCG GGT CGT
                    RF start V 25I   V   A   T   G   Q   P   P   D   P   D   P   K   S   I
GTT ATC GTT GCT ACC GGT CAA CCG CCA GAT CCG GAT CCG AAA TCT ATC
                    RF end                              IIIB start R   I   Q   R   G   P   G   R   A   F   V   T   I   G   K   P
CGT3ATC CAG CGT GGT CCG GGT CGT GCT TTC GTT ACC ATC GGT AAA CCG
                                                        IIIB end P   D   P   D   P   R   S   L   S   I   G   P   G   R   A   F
CCA GAT CCG GAT CCG CGA TCT CTG TCT ATC GGT CCG GGT CGT GCT TTC
    35                  WMJ2 start R   T   R   E   P   P   D   P   D   P   E   E  stop stop stop
CGT ACC CGT GAA CCG CCG GAC CCG GAC CCG GAA GAA TAG TGA TAA GCT
         WMJ2 end
    40
```

FIG. 3

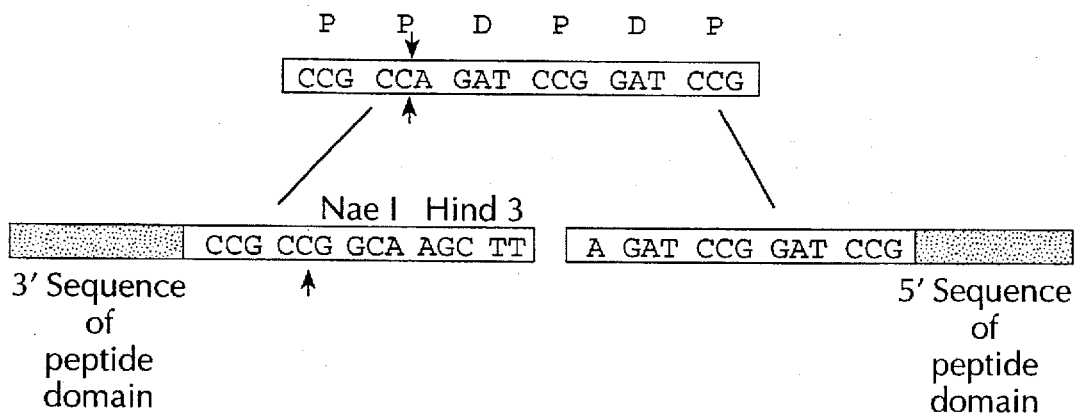

| Domain | Primer Sequence (5'→3') | Polarity |
|---|---|---|
| A | AACGGCTGCAGAATCAAACAGGTCATC | Sense |
| A | AAGCTTGCCGGCGCATCACAACGGATCTGA | Antisense |
| MN | AGATCCGGATCCGAAACGTATCCACATCG | Sense |
| MN | AAGCTTGCCGGCGGGTTTTTGGTGGTAAC | Antisense |
| SC | AGATCCGGATCCGCGATCTATCCAACATC | Sense |
| SC | AAGCTTGCCGGCGGATCACCGGTAGCAACG | Antisense |
| RF | AGATCCGGATCCGAAATCTATCCGTATCA | Sense |
| RF | AAGCTTGCCGGCGGTTGACCGGTAGCAA | Antisense |
| IIIB | AGATCCGGATCCGAAATCTATCCGTATC | Sense |
| IIIB | AAGCTTGCCGGCGGTTTACCGATGGTAACG | Antisense |
| Wmj2 | AGATCCGGATCCGCGATCTCTGTCTATCG | Sense |
| Wmj2 | AAGCTTGCCGGCGGTTCACGGGTACGGA | Antisense |

PRODUCTION OF RECOMBINANT PROTEINS CONTAINING MULTIPLE ANTIGENIC DETERMINANTS LINKED BY FLEXIBLE HINGE DOMAINS

FIELD OF THE INVENTION

The present invention relates to recombinant proteins encoding at least two independent antigenic determinants that are joined by flexible hinge domains. Proteins in this configuration enable presentation of each of the determinants to the immune system and are useful as vaccines against infectious agents, particularly viruses, when many variants of that agent exist. Alternatively, the recombinant proteins of the invention provide a single vaccine effective against diverse infectious agents when the recombinant proteins have antigenic determinants from different infectious agents which are joined by flexible hinge domains. The invention further provides nucleic acids, expression vectors, host cells and methods for production of the subject recombinant proteins.

BACKGROUND OF THE INVENTION

The ability to map antigenic determinants or epitopes with increasing resolution, has advanced the production of vaccines by allowing immunogens to be custom tailored for particular purposes and to eliminate some of the inherent risks in certain types of immunogens. Vaccines made from attenuated viruses or whole killed virus carry the risk that disease-causing mutations could arise in the attenuated virus population or that a few live viruses could remain if viral killing is incomplete. Similar risks occur with other infectious agents when so-formulated in a vaccine. Hence, alternative vaccines formulations have been sought and are being sought.

For example, if the neutralizing epitope of a virus is known, synthetic peptides offer a means to stimulate host immunity to that epitope without the necessity of exposing the host to the infectious agent. Similarly, protein-based, or subunit, vaccines can be produced by purifying a protein from a natural source or producing it recombinantly.

However, the natural complexity of infectious agents, such as seen in viruses capable of rapid mutation to avoid immune surveillance, can complicate the production of vaccines. To effectively combat such agents, a new or separate vaccine may be needed for each isolate or strain of the infectious agent. Undertaking production and testing of a different synthetic peptide or recombinant protein for every isolate, is time consuming and expensive. Consequently, alternate approaches to vaccine production are necessary.

The present invention provides one such approach for vaccine development. The subject recombinant proteins contain several antigens from different isolates or strains of a single infectious agent, with the antigens in a spatial arrangement which permits the individual antigens to stimulate an immune response. Hence, multiple epitopic variants of the same antigenic site can be provided in a single vaccine preparation. There are numerous advantages to the subject invention. First, the proteins can encode the relevant epitopes without deleterious sites involved in causing disease or infection. Second, a single vaccine product is available to combat multiple infectious agents that cause the same disease. Third, if the antigenic epitopes are from different disease-causing infectious agents, then a single vaccine can serve as a combination vaccine to replace the several vaccines normally needed to prevent multiple infections. Fourth, the expense of producing a different vaccine for each strain or substrain of a pathogen is reduced. Finally, by producing such proteins via recombinant DNA technology, new vaccines can be rapidly developed and existing vaccines can be altered with relative ease in response to changes in infectious agents, i.e. as new strains or isolates of pathogens are discovered.

SUMMARY OF THE INVENTION

The present invention relates to recombinant proteins composed of at least two peptide domains and at least one spacer domain arranged in the order peptide domain-spacer domain-peptide domain, and when additional peptide or spacer domains are present, such domains are added sequentially thereto in alternating order beginning with a spacer domain. The peptide domain can be a peptide antigen, a viral cell receptor binding site, a helper T cell site or a cytotoxic T cell recognition site; whereas the spacer domain is an amino acid sequence which is capable of forming a flexible hinge that allows the peptide domains to be recognized by the immune system of a mammal and either (i) to stimulate antibody formation to one or more of said peptide domains, (ii) to induce a helper T cell immune response or (iii) to stimulate a cytotoxic T lymphocyte (CTL) response.

In particular, the peptide antigen is from a virus, bacterium, parasite, fungus or protein. For example, these antigens can be neutralizing epitopes or epitopes from a known site of antigenic variation from one or more different viruses, i.e. the peptide antigens can be totally unrelated epitopes. Likewise, these antigens can be epitopic variants of the same site of antigenic variation, i.e., the peptide antigens can be related epitopes. In one embodiment, the peptide antigens are from the $V_3$ loop of HIV-1 isolates MN, SC, RF, IIIB or WMJ2. In another embodiment, the peptide antigens are from the $V_3$ loop consensus sequences from HIV-1 clades A-E and S. When the peptide domain is a helper T cell site, it is preferably an amino acid sequence from the $CD_4$ binding domain of the HIV env protein which is capable of inducing a helper T cell response.

The flexible hinge of the spacer domain permits the peptide domains to be independently presented to and recognized by the immune system. Such flexibility can be provided by amino acid sequences of the immunoglobulin heavy chain hinge regions or modifications thereof. For example, such sequences can be proline rich; in one embodiment of the invention, a spacer domain is provided by the sequence Pro-Pro-X-Pro-Y-Pro, (SEQ ID NO:7) wherein X or Y are independently any amino acid. In a preferred embodiment, X and Y are aspartic acid. The multiple epitope AIDS vaccine (MEAV) protein depicted in FIGS. 1 and 2 is an example of a recombinant protein of this invention.

Another aspect of the invention provides an isolated nucleic acid encoding the recombinant proteins of the invention, replicable expression vectors and host cells containing such nucleic acids. The invention further provides a method of using the expression vectors to produce the subject recombinant proteins.

Yet another aspect of this invention provides a method of vaccination against HIV by administering an immunogenic amount of a recombinant protein having peptide domains which are epitopic variants from the $V_3$ loop of HIV isolates or clades, wherein said amount is effective to elicit neutralizing antibodies to HIV. In one embodiment, the recombinant protein is MEAV. Pharmaceutical compositions containing such proteins are also provided.

BRIEF DESCRIPTION OF THE DRAWINGS

FIG. 2 shows the nucleotide and amino acid sequences of the recombinant MEAV gene (SEQ ID NO:8). The extent and sequence for each peptide domain is indicated; spacer domains are underlined.

FIG. 3 illustrates a general strategy for designing DNA cassettes with peptide and spacer domains by PCR amplification. The PCR primers used in synthesis of peptide domains with the partial spacer domains at the ends which facilitated cassette assembly of the MEAV gene are shown. The sequences depicted in this figure have the following sequence identification numbers: CCG CCA GAT CCG GAT CCG is SEQ ID NO:58; CCG CCG GCA AGC TT is SEQ ID NO:59; A GAT CCG GAT CCG is SEQ ID NO:60; the oligonucleotides designated as A-Sense, A-Antisense, MN-Sense, MN-Antisense, SC-Sense, SC-Antisense, RF-Sense, RF-Antisense, IIIB-Sense, IIIB-Antisense, Wmj2-Sense and Wmj2-Antisense are SEQ ID NOS: 61–72, respectively; and PPDPDP is SEQ ID NO:73.

Figure 5:
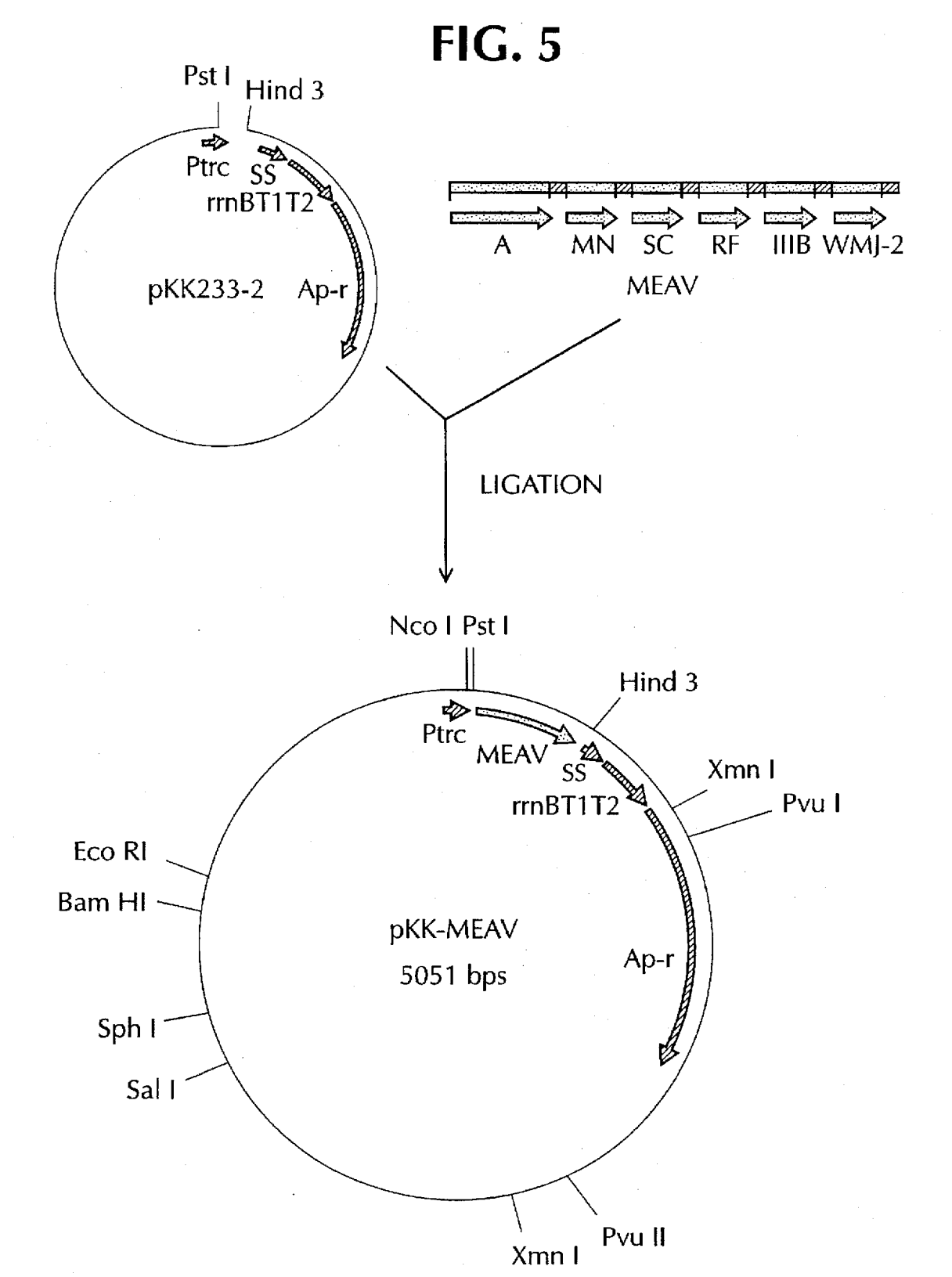

FIG. 5 illustrates the construction of the expression vector pKK-MEAV by ligating a PstI-HindIII fragment from pMEAV into the expression vector pKK233-2 digested with PstI and HindIII.

FIG. 7 is a graphic illustration of the antibody response as determined by enzyme immunoasssay (EIA) from a guinea pig immunized with the MEAV protein. Microtiter plates were coated with peptides representing the IIIB (open square), MN (open circle), SC (solid circle), CD4 (solid square), RF (open triangle), or WMJ2 (solid triangle) regions of the MEAV protein and reacted with anti-MEAV antiserum. The plot indicates the titer of serum which gave a positive signal of 0.5 $OD_{492}$ for each peptide. MEAV protein was injected into the guinea pig at the times indicated by the arrows.

DETAILED DESCRIPTION OF THE INVENTION

Figure 1:
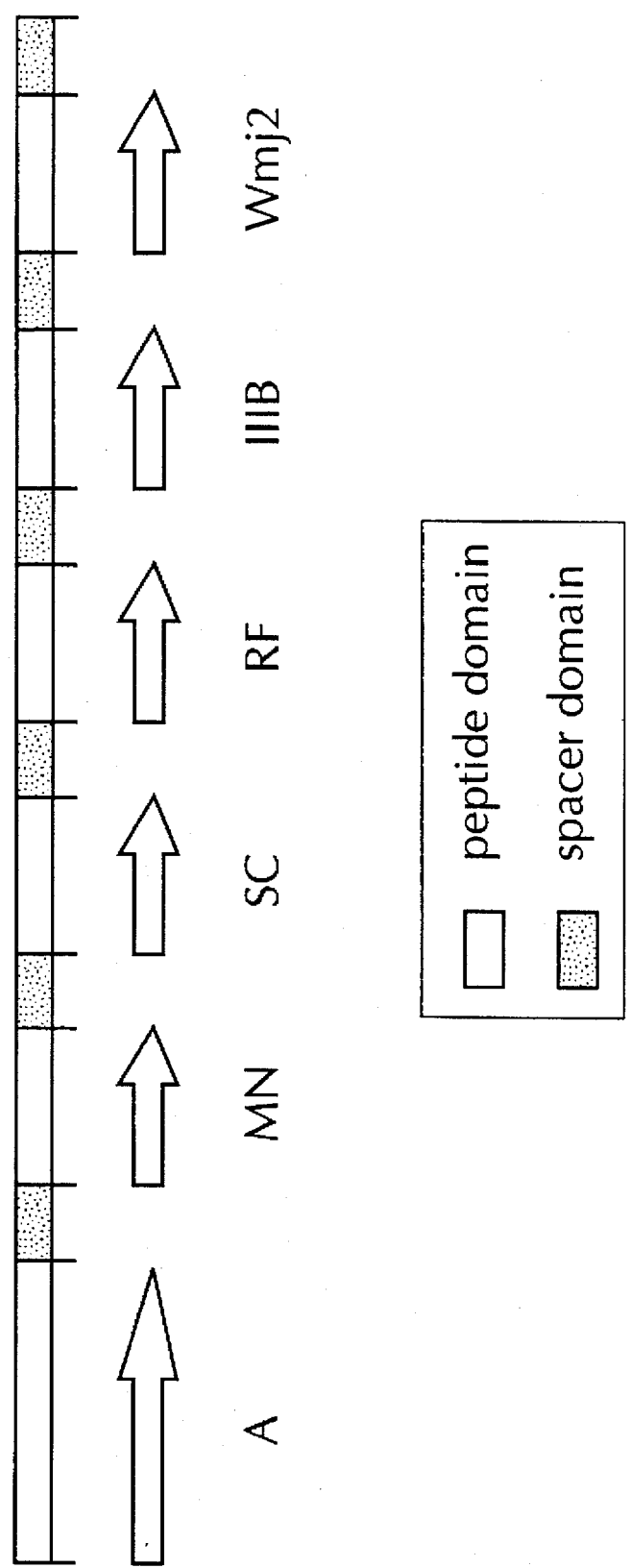
FIG. 1 depicts a schematic diagram of the synthetic MEAV gene encoding a portion of the CD9 binding domain (A) and five V₃ loop epitopes from HIV-1 (MN, SC, RF, IIIB and WMJ2). The solid boxes encode spacer domains.

The present invention relates to recombinant proteins containing multiple epitopes (i.e. multiple antigenic determinants) in peptide domains linked by flexible hinge (spacer) domains. In accordance with this invention, separation of the peptide domains by flexible hinge domains permits the peptide domains to be accessible to the immune system. Since the antigenic determinants of the peptide domains are accessible, an immune response can be generated to a peptide domain. Such artificial protein constructs can thus be used to simultaneously stimulate an immune reaction to a variety of antigenic sites, to stimulate a helper T cell response, or a CTL response. For example, if the peptide domains contain neutralizing epitopes from different HIV isolates, then a single protein can be developed into a vaccine to provide immunity against several HIV isolates. In another embodiment, each peptide domain of the artificial protein can encode a neutralizing epitope from a different virus or bacterium. Again a single immunogenic protein can produce a vaccine effective against several different viruses or pathogens. In contrast, a traditional vaccine requires a separate component (killed virus, protein, peptide, etc.) for each HIV isolate, each different virus or each different pathogen. The subject recombinant proteins thus simplify and reduce the cost of vaccine production.

The recombinant proteins of this invention are composed of at least two peptide domains and at least one spacer domain arranged in the order peptide domain-spacer domain-peptide domain. When additional peptide or spacer domains are present, such domains are added sequentially to the core structure in alternating order beginning with a spacer domain. The last domain of the protein can be either a spacer or peptide domain.

The peptide domain comprises a peptide antigen, a viral cell receptor binding site, a helper T cell site or a cytotoxic T cell recognition site; whereas the spacer domain encodes an amino acid sequence which is capable of forming a flexible hinge that allows the peptide domains to be independently recognized by the immune system of a mammal and (i) to stimulate antibody formation to one or more of said peptide domains, (ii) to induce a helper T cell immune response or (iii) to stimulate a cytotoxic T lymphocyte (CTL) response.

Accordingly, the recombinant proteins of the present invention can contain from 2 to about 25 peptide domains, preferably from about 3 to about 15 peptide domains and even more preferably from about 5 to about 10 peptide domains. Each of the peptide domains can have from about 5 to about 100 amino acid residues, preferably from about 8 to about 50 amino acid residues, and even more preferably from about 10 to about 35 amino acid residues.

When the peptide domain is a peptide antigen, such antigen can be from a virus, bacterium, parasite, fungus or protein (e.g. a tumor antigen). Such viruses include human immunodeficiency virus (HIV), hepatitis C virus (HCV), influenza virus, Dengue virus, human papilloma virus (HPV), rotavirus, Epstein-Barr virus (EBV), varicella zoster virus, chicken pox virus, herpes simplex viruses, roseola virus (herpes simplex virus 6), measles virus, respiratory syncytia virus, human T lymphotrophic virus I (HTLV I), human T lymphotrophic virus II (HTLV II), mumps virus, polio virus and the like. The HIV virus includes HIV-1 and HIV-2 or any isolate of HIV. For example, HIV-1 isolates include the HIV viral isolates designated as MN, RF, SC, IIIB, WMJ2 or any of the over 200 known HIV isolates [Meyers et al., eds., (1992) Human Retroviruses and AIDS. Pub. Theoretical Biology and Biophysics Group T-10, Los Alamos National Laboratory, Los Alamos, N. Mex]. In a preferred embodiment the peptide antigen is from an HIV isolate or an HIV clade (see below).

Bacteria include bordetella, mycobacteria, chlamydia, gonococcus and the like. Parasites include trypanosomes, plasmodia and the like. Proteins include tumor antigens from viral or cellular sources.

Further, the peptide antigen can be a neutralizing epitope or an epitope from a known site of antigenic variation from one or more of the same or different viruses. As used herein, a "neutralizing epitope" is an epitope which elicits an immune response that is capable of preventing or attenuating the disease or condition(s) caused by an infectious agent or pathogen. The subject recombinant proteins allow preparation of immunogens which contain several related epitopes from a virus with a known site of antigenic variation. Viruses with known sites of antigenic variation include HIV, HCV, influenza virus, Dengue virus, RSV and HPV. The molecular identity of some of the important sites of antigenic variation are known for HIV, HCV and influenza virus. For example, the influenza virus hemagglutinin (HA) protein has known sites of antigenic variation for different influenza strains. Similarly, HIV-isolates exhibit marked variability at the $V_3$ loop region of the env protein (gp120), a site known to elicit neutralizing antibodies against HIV-1 isolates. In this regard, related HIV-1 isolates have been classified into clades. There are 5 principal known clades designated A–E. S is an overall consensus sequence of all of the known clades. The consensus sequence for the $V_3$ loop region of these clades is shown in Table 1 together with the sequences of selected HIV-1 isolates.

TABLE 1

$V_3$ loop region sequences of HIV-1 clades and selected HIV-1 isolates

| CLADE[1] or ISOLATE | SEQUENCE[2] | SEQ ID NO: |
|---|---|---|
| B | ESVEINCTRPNNNTRKSIHIGPGRAFYTTGEM | 9 |
| (S) | ------------------------Q---A--D- | 10 |
| A | KP-R--------------V-----QT--A--D- | 11 |
| C | -----V----------R----QT--A--D- | 12 |
| D | ---T------Y----QRT-----Q-L----R- | 13 |
| E | K---------S-----T--T----QV--R--D- | 14 |
| RWANDA | KA-K-------KT---GVR----Q-W-AR-N- | 15 |
| BMN[b] | ---Q-------Y-K--R------------KN- | 16 |
| SC[b] | -A------------TR-----------A--D- | 17 |
| 6016a[b] | -------------------M---S---A--D- | 18 |
| 6000C01[b] | -T-K---A-L-----R--PV---K-L-----D- | 19 |
| D747[c] | Q----VY---------GVR----QT--A--D- | 20 |
| 5414[d] | K-I A-T-----Y----QRTR--S-Q------R- | 21 |
| 8683C01[e] | K---------S-----T---P----QV--R--D- | 22 |
| 8101C01[b] | --------------------L----Q-W----Q- | 23 |
| 8621C01 | -T---------S----------L-W------A---- | 24 |
| 7932dC01 | ------------S---------M-W--------A- | 25 |
| WMJ2[b] | -----------Y--V-R-LS--------.R-R-- | 26 |
| ELI | ---K-T-A--YQ---QRTP--L-QSL---RS- | 27 |
| YU2 | ---V---------------N------L------ | 28 |
| NY2 | K------------K-G-A-----TL-AREK- | 29 |
| V772 | DP-N-T-----S---------A---V-HA---- | 30 |
| MAL | -T-T-------G----RG--F---Q-L-----.- | 31 |
| 8225 | KP-R----------EGVG----QT--K--N- | 32 |
| 5418[d] | ---T-------YS---QGT-------YC-S-Y- | 33 |
| 5422[d] | --I P-------YS---QRTP--L-Q-L---RT- | 34 |
| 7934C01 | ---V-----H---------V-W--SLF----- | 35 |

[1]The first five entries in this column are HIV-1 clades and 5 is a consensus sequence; the remaining entries are HIV-1 isolates. The superscripts indicate the clade to which the isolates belong (where known).
[2]The sequences of the clades represent consensus sequences; all others are sequences of the particular isolate. The dashes represent sequence identities; the dots represent a missing residue.

The peptide antigens have amino acid sequences from neutralizing epitopes, from epitopic variants or from other antigenic sites. Antigens containing epitopes can be composed of continuous or discontinuous sequences. Besides the residues involved in stimulating the immune response, the peptide antigen can include additional residues (or sequences). For example, additional residues may be necessary to present the epitope or antigen in the proper conformation for recognition by the immune system. In accordance with this invention, a peptide antigen comprises a sufficient number of amino acid residues to act as an immunogen (i.e., elicit an immune response), but is not strictly limited to any particular number of amino acids.

The peptide antigens can also include analogues of known epitopes or antigenic determinants. Hence, one of ordinary skill in the art can make adjustments for conservative substitutions in the sequences and select among the alternatives where non-conservative substitutions are involved in the prescribed or known sequences. The peptide antigens can therefore comprise substitutions, insertions and/or deletions of amino acids of known sequences as long as the immunoreactivity of the epitope is preserved.

In a preferred embodiment, the peptide antigens are from the $V_3$ loop of an HIV-1 clade, an HIV-1 isolate or modifications thereof that are capable of stimulating immune responses to the respective epitopes (see Table 1). In an one embodiment the peptide antigens are from the $V_3$ loop of HIV-1 isolates MN, SC, RF, IIIB or WMJ2 and have the amino acid sequences of SEQ ID NO:1, SEQ ID NO:2, SEQ ID NO:3, SEQ ID NO:4 and SEQ ID NO:5, respectively.

When the peptide domain is a helper T cell site, it is preferably an amino acid sequence from the CD4 binding site of the HIV env protein which is capable of inducing a helper T cell response. The amino acid sequence of the helper T cell site includes analogues as defined above for peptide antigens, provided that the ability to induce a helper T cell response is preserved. In a preferred embodiment the helper T cell site has the amino acid sequence of SEQ ID NO:6.

Viral cell receptor binding in conjunction with antigen binding can enhance or augment the immune response to that antigen. Hence, when the peptide domain is a viral cell receptor binding site, then the domain comprises an amino acid sequence capable of binding to a viral cell receptor, particularly to receptors in the immunoglobulin superfamily. The immunoglobulin superfamily is a group of molecules with receptor or adhesion functions and are typically, but not only, found on lymphocytes [Hunkapillar et al. (1986) *Nature* 323:15; Williams (1987) *Immunol. Today* 8:298]. The amino acid sequence of a viral cell receptor site includes analogues as defined above for peptide antigens, provided that the ability to induce or augment an immune response is preserved. Viral cell receptor binding sites include viral attachment peptides which are effective as immune stimulators.

When the peptide domain is a cytotoxic T cell recognition site, it includes analogues as defined above for peptide antigens, provided that the ability to stimulate a CTL response is preserved.

The peptide domains of the present invention are recognized by the immune system of a mammal and either (i) stimulate antibody formation to one or more of said peptide domains, (ii) induce a helper T cell immune response or (iii) stimulate a cytotoxic T lymphocyte (CTL) response. The measurement of specific antibodies, helper T cell responses or CTL responses can be determined by techniques known in art. For example, the subject recombinant protein is injected one or more times into an animal to elicit an immune response. The serum from that animal is then tested for the presence of specific antibodies against one or more of the peptide domains present in the recombinant protein. Alternatively, the helper T cell or CTL activity generated by the serum can be measured. Methods for measuring antibody responses such as EIA, immunoprecipitation, radioimmunoassay, immunoblotting (or Western blotting) and the like are described in Harlow et al. (1988) *Antibodies: A Laboratory Manual*, Cold Spring Harbor Laboratory Press, Cold Spring Harbor, N.Y., 726 pp. Methods for measuring helper T cell responses and CTL responses are described in Mishell et al. (1980) *Selected Methods in Cellular Imunnology*, W. H. Freeman and Company, San Francisco, Calif., pp.486; Shinohara (1992) in *Encyclopedia of Immunology* (Roitt et al., eds.), Academic Press, London, p. 451; Fitch (1992) in *Encyclopedia of Immunology* (Roitt et al., eds.), Academic Press, London, p. 654; and Coligan et al., eds. (1992) *Current Protocols in Immunology*, John Wiley & Sons, New York, N.Y..

The flexible hinge of the spacer domain permits the peptide domains to be independently presented to and recognized by the immune system. Such flexibility can be provided by amino acid sequences of the immunoglobulin heavy chain hinge regions or modifications thereof. The sequences of immunoglobulin hinge regions are known in the art, for example, in Hasemann et al. (1989) in *Fundamental Immunology, Second Edition* (Paul, ed.) Raven Press Ltd., New York, N.Y., pp. 209–233. The regions of these sequences which impart flexibility to a spacer domain (i.e. a stretch of amino acids) are typically proline rich. Accordingly, in one embodiment of the invention, a spacer domain is provided by the sequence Pro-Pro-X-Pro-Y-Pro (SEQ ID NO:7), wherein X or Y are independently any amino acid. When X and Y are Cys and Ala, respectively, then the flexible hinge is from a human $\gamma$ immunoglobulin heavy chain. When X and Y are Thr and Ser, respectively, then the flexible hinge is from a human $\alpha_1$ immunoglobulin heavy chain. In a preferred embodiment, X and Y are aspartic acid.

In a one embodiment, a recombinant protein of this invention is the MEAV protein depicted in FIGS. 1 and 2.

Another aspect of this invention provides a nucleic acid encoding the recombinant proteins of the invention. Thus, the proteins of the present invention are prepared by recombinant DNA techniques. In general, the amino acid sequences of the peptide and spacer domains are determined and then reversed translated into the appropriate nucleic acid codes. Because of the degeneracy of the genetic code, several codons may be available to encode certain amino acids. Thus, codons are selected to provide optimal codon usage in the host expression system and thereby maximize expression. While the majority of the codons selected in reverse translation are those that are optimal for the host system, when necessary less optimal codons are used to generate convenient restriction sites which facilitate cloning or construction of the gene encoding the subject recombinant proteins. Similarly, less optional codon usage can be employed to reduce nucleic acid sequence redundancy and minimize repeated sequences.

The general techniques used for the subject invention, especially for cloning, performing the polymerase chain reaction (PCR), sequencing clones, synthesizing oligonucleotides, constructing expression vectors, transforming cells, inducing protein expression, growing cells in culture, and the like are known in the art and laboratory manuals are available describing these techniques. Hence, the present invention employs, unless otherwise indicated, conventional techniques of molecular biology, microbiology, cell culture and recombinant DNA which are with the skill of the ordinary artisan. Examples of useful laboratory manuals include Sambrook et al. (1989) *Molecular cloning: A Laboratory Manual*, 2nd Ed., Cold Spring Harbor Laboratory Press, Cold Spring Harbor, N.Y.; and Miller et al. (1987) *Gene Transfer Vectors for Mammalian Cells*, Cold Spring Harbor Laboratory Press, Cold Spring Harbor, N.Y.

The following general definitions apply to the present invention. More specific definitions for various aspects of the present invention are also provided herein.

The term "polynucleotide" or "nucleic acid" as used herein refers to a polymeric form of nucleotides of any length, either ribonucleotides or deoxyribonucleotides. This term refers only to the primary structure of the molecule. Thus, this term includes double- and single-stranded DNA, as well as double- and single-stranded RNA. It also includes known types of modifications, for example, nucleic acid labels which are known in the art, methylation, "caps", substitution of one or more of the naturally occurring nucleotides with an analog.

The term "recombinant nucleic acid" as used herein means a nucleic acid of genomic, semisynthetic, or synthetic origin which, by virtue of its origin or manipulation: (1) is not associated with all or a portion of a polynucleotide with which it is associated in nature, (2) is linked to a polynucleotide other than that to which it is linked in nature, or (3) does not occur in nature. As used herein "an isolated nucleic acid" refers to DNA or RNA which has been purified to a degree suitable for manipulation by recombinant DNA techniques or has been purified to homogeneity. The purity of a nucleic acid can be determined by conventional techniques, including but not limited to, chromatography and electrophoresis. Similarly, whether a nucleic acid is of a purity sufficient for recombinant DNA techniques can be assessed by its positive performance in an assay relative to a control nucleic acid.

"Recombinant host cells", "host cells", "cells", "cell lines", "cell cultures", and other such terms denoting microorganisms or higher eukaryotic cell lines cultured as unicellular entities refer to cells which are, can be, or have been, used as recipients for recombinant expression vectors or other transferred DNA, and include the progeny of the original cell which has been transfected or transformed. It is understood that the progeny of a single parental cell is not necessarily completely identical in morphology or in genomic or total DNA complement as the original parent, due to natural, accidental, or deliberate mutation.

"Control sequence", "regulatory element", and "regulatory region" refer to polynucleotide or nucleic acid sequences which are necessary to effect the expression of the coding sequences of the gene products to which they are operably joined. The control sequence can act to control expression at the level of transcription, translation, post-translational processing, post-translational modification, secretion or any other step in production of a gene product. The nature and number of such control sequences needed for expression differs depending upon the host organism but can be readily determined by one of ordinary skill in the art. In eukaryotes, generally, such control sequences include promoters, terminators and, in many instances, enhancers. The term "control sequences" is intended to include, at a minimum, all sequences whose presence is necessary for expression, and may also include additional sequences whose presence is advantageous, for example, leader sequences, terminators, enhancers and other regulatory sequences. In prokaryotes, such control sequences include promoters, TATA boxes and terminators.

"Operably linked" refers to a juxtaposition of sequence elements, regulatory elements, control sequences and the like with coding sequences for a gene product, wherein the elements so described are joined one to another in a relationship permitting them to function in their intended manner, e.g. to control expression. A control sequence "operably linked" to a coding sequence is spatially joined in such a way that expression of the coding sequence is achieved under conditions compatible with the control sequences. In particular, the subject regulatory elements, as many as are necessary or desired, are typically joined to the coding sequence of a gene product to achieve the controlled expression of that gene product consistent with the function (capability) of the selected regulatory elements.

A "coding sequence" is a polynucleotide sequence which is transcribed into mRNA and/or translated into a polypeptide when placed under the control of appropriate regulatory sequences. A coding sequence encodes a gene product. The boundaries of the coding sequence are determined by a translation start codon at the 5'-terminus and a translation stop codon at the 3'-terminus of the sequence. A coding sequence can include, but is not limited to mRNA, cDNA, and recombinant polynucleotide sequences. As used herein, a coding sequence may be used to refer to a nucleic acid which, optionally, includes introns.

"Transformation", as used herein, refers to the insertion of an exogenous polynucleotide or recombinant nucleic acid into a host cell, irrespective of the method used for the insertion, for example, direct uptake, lipid-mediated transfection, transfection, transduction, f-mating or electroporation. The exogenous polynucleotide may be maintained as a non-integrated vector, for example, a plasmid, or alternatively, may be integrated into the host genome.

Yet another aspect of the present invention provides replicable expression vectors having the coding sequences of the subject recombinant proteins operably linked to control sequences and regulatory regions that enable protein production in a host system. Similarly, the host cells containing these expression vectors are also provided by the invention. A large number of expression systems are known in the art and an appropriate system can be readily determined by one of ordinary skill in the art. For example, the subject recombinant proteins can be expressed in bacterial expression systems such as E. coli, in yeast systems, in animal virus systems, in baculovirus systems or mammalian cell culture systems. The choice of systems depends on many factors including the desired post-translational modifications or whether secretion is desired. In a preferred embodiment, an E. coli expression system is used with the coding sequence under control of the trc promoter.

Further, the subject recombinant proteins can be expressed in viral vectors that are used as live or recombinant vaccines. Such vectors include pox virus-based vectors such as vaccinia virus [Moss (1991) Science 252:1662–1667], adenovirus-based vectors [Graham (1990) TIBTECH 8:85–87; Prevec et al. (1989) J. Gen. Virol. 70:429–434], herpes virus-based vectors [Liang et al. (1992) Virology 189:629–639] and Salmonella species-based vectors.

Vector construction employs techniques which are known in the art. Oligonucleotides can be synthesized which encode part or all of the coding sequences of the peptide or spacer domains. The techniques for chemical or enzymatic synthesis of oligonucleotides are well known in the art. Fragments encoding peptide or spacer domains can be obtained from cloned DNA. Site-specific DNA cleavage is performed by treating DNA with suitable restriction enzymes under conditions which generally are specified by the manufacturer of these commercially available enzymes. The cleaved fragments can be separated using polyacrylamide or agarose gel electrophoresis techniques, according to the general procedures found, for example, in Methods of Enzymology (1980) 65:499–560. Fragments can also be produced by PCR using primers which are complementary to the ends of the fragment to be amplified. Optionally, if additional sequences are included in the primers, these sequences can be incorporated at the end(s) of the fragment during PCR.

Sticky-ended DNA fragments can be converted to blunt-ended fragments using E. coli DNA polymerase 1 (Klenow) in the presence of the appropriate deoxynucleotide triphosphates (dNTPs) in the mixture. Alternatively, treatment with S1 nuclease can also be used, resulting in the hydrolysis of any single-stranded DNA portions.

Ligations are carried out using standard buffer and temperature conditions with a ligase, (typically T4 DNA ligase and ATP); sticky-end ligations require less ATP and less ligase than blunt-end ligations. When vector fragments are used as part of a ligation mixture, the vector fragment is often treated with bacterial alkaline phosphatase (BAP) or calf intestinal alkaline phosphatase to remove the 5'-phosphate and thus prevent religation of the vector; alternatively, restriction enzyme digestion of unwanted fragments can be used to prevent undesired ligation products. If necessary any nucleotide gaps can be filled in using the polymerase extension reaction prior to ligation.

Ligation mixtures are transformed into suitable cloning hosts, such as E. coli, and successful transformants selected by, for example, antibiotic resistance, and screened for the correct construction. Screening methods are well known and include identifying restriction enzyme digestion patterns as well as sequencing of the construct.

Host cells include the prokaryotic hosts and eukaryotic hosts used in vector construction, testing and in protein expression.

Vectors are introduced by transformation into the appropriate host. Transformation may be by any known method for introducing polynucleotides into a host cell, including, for example, packaging the polynucleotide in a virus and transducing a host cell with the virus, or by direct uptake of the polynucleotide or vector. The transformation procedure used depends upon the host to be transformed. Bacterial transformation by direct uptake generally employs treatment with calcium or rubidium chloride. Yeast transformation can be by direct uptake. Mammalian transformations by direct uptake may be conducted using the calcium-phosphate precipitation method or the various known modifications thereof. Transformation methods are provided, for example, by Sambrook et al.

Prokaryotic hosts are preferably used during construction of the subject expression vectors as well as for expression. Eukaryotic host cells are preferably used for expression of the subject recombinant proteins. Among prokaryotic hosts, E. coli is most frequently used but any suitable host can be used. Transfer vectors compatible with prokaryotic hosts are commonly derived from, for example, pBR322, a plasmid that contains operons conferring ampicillin and tetracycline resistance, and from various pUC vectors, which also contain sequences conferring antibiotic resistance markers. These markers may be used to identify successful transformants by selection for antibiotic resistance.

Eukaryotic hosts include yeast, insect and mammalian cells, Saccharomyces cerevisiae and Saccharomyces carlsbergensis are the most commonly used yeast hosts. Yeast compatible vectors carry markers which permit selection of successful transformants by conferring prototrophy to auxotrophic mutants or resistance to heavy metals on wild-type strains. Control sequences for yeast vectors are known in the art and include promoters for the synthesis of glycolytic enzymes, including the promoter for 3-phosphoglycerate kinase. Terminators can also be included, such as those from the enolase gene. Insect cell lines and viral vectors from the baculovirus system can be employed to express the subject recombinant proteins.

Mammalian cell lines available as hosts for expression are known in the art and include many immortalized cell lines available from the American Type Culture Collection (ATCC), including HeLa cells, Chinese Hamster ovary (CHO) cells, baby hamster kidney (BHK) cells, and a number of other cell lines. Suitable promoters for mammalian cells are also known in the art and include viral promoters such as those from Simian Virus 40 (SV40), Rous sarcoma virus (RSV), adenovirus (ADV), and bovine papilloma virus (BPV). Similarly heat shock promoters are known to be useful. Mammalian cells can also require terminator sequences and poly A addition sequences. Enhancer sequences which increase expression and sequences which cause amplification of the gene can also be included, if desirable. These sequences are known in the art. Vectors suitable for replication in mammalian cells may include viral replicons, or sequences which insure integration of the appropriate sequences into the host genome.

In a further aspect, the present invention provides a method of producing a recombinant protein which comprises cultivating a microorganism or host cell transformed by an expression vector of the invention for a time and under conditions sufficient to express said protein and recovering said protein. After construction of the vector, and transformation of the appropriate expression host, the host is cultivated under conditions which depend on both the host and the expression system. Such conditions are well known in the art and depend on the selected expression systems. Any optimization of expression, if necessary, can be readily accomplished by the ordinarily skilled artisan. For example with the E. coli trc promoter system, cells are grown to mid log phase, IPTG is added to induce expression and cell growth is continued for several hours. At the end of that time the cells are harvested and analyzed to determine if the recombinant protein was produced. Protein production can be assessed by many ways, including appearance of a new band on a gel, by Western blotting, by ELISA (enzyme-linked immunoassay), radiolabeling or other techniques. After expression is established the protein is recovered by purification using chromatography, electrophoresis, HPLC, precipitation, or any of a variety of protein purification methods.

A still further aspect of the invention relates to a method of using the recombinant proteins of the present invention for treating or preventing HIV infection by administering an amount of a recombinant protein having peptide domains that encode HIV peptide antigens effective to treat HIV infection or to elicit immunoprotective antibodies against HIV infection. Neutralizing antibodies are immunoprotective. The MEAV protein exemplifies a recombinant protein which elicits neutralizing antibodies to HIV.

Accordingly, the recombinant proteins for treating or preventing HIV infection can be formulated as a vaccine composition using adjuvants, pharmaceutically-acceptable carriers or other ingredients routinely provided in vaccine compositions. Such formulations are readily determined by one of ordinary skill in the art and include formulations for immediate release and for sustained release, e.g., microencapsulation. The present vaccines can be administered by any convenient route including subcutaneous, oral, intramuscular, intravenous, or other parenteral or enteral route. Similarly the vaccines can be administered as a single dose or divided into multiple doses for administration.

The vaccine compositions of the instant invention contain an immunoeffective amount of the subject recombinant protein (with HIV peptide antigens), and a pharmaceutically acceptable carrier, to treat or prevent HIV infection. Such compositions in dosage unit form can contain about 0.5 µg to about 1 mg of the protein per kg body weight. When delivered in multiple doses, the dosage unit form is conveniently divided into the appropriate amounts per dosage.

The following examples further illustrate the invention.

EXAMPLE 1

Materials and Methods

A. General recombinant DNA methods: Unless otherwise stated, standard recombinant DNA methodology was followed as described in Maniatis et al. (1982) *Molecular Cloning: A Laboratory Manual*, Cold Spring Harbor Laboratory Press, Cold Spring, N.Y., pp. 545; Sambrook et al. (1989); Ausubel et al. (1989) *Current Protocols in Molecular Biology*, Green Publishing Associates and Wiley-Interscience, New York, N.Y. and Innis et al. (1989) *PCR Protocols: A Guide to Methods and Applications*, Academic Press, Inc., San Diego, Calif., pp. 482.

Plasmid DNA was prepared from colonies using the alkaline lysis method or equilibrium centrifugation in cesium chloride.

Dideoxy sequencing from plasmid DNA was performed with a kit from United States Biochemical, Inc., according to manufacturer's instructions. All plasmid constructs were verified by sequencing.

The recipient bacterial strain for the cloning procedures was *E. coli* $MM_{294}$ (endA ThiA hsdR17 supE44) and the recipient strain for protein expression was *E. coli* BL21 ($F^-$ompT $r_B^-$ $m_B^-$)

B. Oligonucleotide preparation: Oligonucleotides (0.2 or 1.0 μmol) were synthesized on a Model 8600 DNA Synthesizer (Biosearch, Inc.) according to the manufacturer's instructions using cyanoethyl phosphoramidites on solid phase controlled pore glass (CPG) columns.

The oligonucleotides were de-protected and removed from the CPG support by incubating the oligonucleotide-bound CPG beads from the column for at least 5 hours at 55° C. in 500 ml of concentrated $NH_4OH$. The beads were allowed to settle and the supernatant was passed over a 25 ml PD-10 column (Pharmacia LKB Biotechnology Inc.) equilibrated in distilled water ($dH_2O$). The oligonucleotide was eluted with $dH_2O$ and 1 ml fractions were collected. Peak fractions were identified by absorbance, combined and precipitated with 1/10 volume of 3M LiCl and 2½ volumes of ethanol in a dry ice-ethanol bath for 1 h. The precipitate was pelleted, dried and suspended in water at the desired concentration.

To phosphorylate an oligonucleotide, 5 units of $T_4$ polynucleotide kinase were added to 10 g of oligonucleotide in 100 μl of kinase buffer (70 mM Tris-HCl, pH7.6, 10 mM $MgCl_2$, 100 mM KCl, 5 mM DTT, 500 μg/ml BSA, 10 mMATP). The reaction was incubated at 37° C. for 60 min followed by heat inactivation at 90° C. for 10 min.

After phosphorylation, the oligonucleotide was gel purified. One absorbance unit of the phosphorylated oligonucleotide was mixed with 1/5 volume of 6× loading buffer (10 mM Tris, 10 mM EDTA, 1 mM borate, 0.1% bromophenol blue, 50% glycerol) in a final volume of 40 μl and heated at 90° C. for 5 minutes before loading on a 1.0 mm thick denaturing polyacrylamide gel (15% acrylamide, 0.6% bisacrylamide, 7M urea in 1×TBE). The gel was pre-run at 500 volts for 1 h before loading and the samples were electrophoresed at the same voltage for 4 h. Gel bands were visualized by UV shadowing and oligonucleotides were excised from the gel, transferred to micro-test tubes and soaked in oligonucleotide elution buffer (0.5M ammonium acetate, 1 mM EDTA and 0.1% SDS) overnight at 37° C. The solution was transferred to a clean tube and the oligonucleotide precipitated at −70° C. for 1 h with 2½ volumes of ethanol. The precipitate was collected by centrifugation in an Eppendorf microfuge for 10 min, washed in 75% ice-cold ethanol, and dried. The purified oligonucleotide was redissolved in the desired volume of $dH_2O$.

Oligonucleotide concentrations were determined by $O.D._{260}$.

C. Annealing and ligation: An equal molar ratio (0.1–0.5 μmol) of the gel-purified oligonucleotides in each construct was mixed with about 1/10 molar ratio of restriction enzyme-digested DNA vector in a volume of 20 μl, heated to 90° C. for 5 min and slowly cooled to room temperature over a period of 1 h. Ligation was initiated by mixing the annealing mixture, 10× ligase buffer and $dH_2O$ for a final reaction volume of 50 μl in 66 mM Tris-HCl, pH 7.6, 6.6 mM $MgCl_2$, 10 mM DTT and 1 mM ATP. Ten units of $T_4$ DNA ligase were added and the mixture was incubated overnight at 15° C.

When necessary, nucleotide gaps between partially complementary oligonucleotides or vectors were filled by a polymerase extension prior to ligation.

The phosphorylated oligonucleotides and restriction enzyme-digested DNA vector (in the same ratios as above) were mixed with 10× annealing buffer and $dH_2O$ in a final volume of 25 μl in 10 mM Tris-HCl, pH 7.5, 2 mM $MgCl_2$ and 50 mM NaCl. The reaction mixture was heated to 75° C. for 5 min and slowly cooled to room temperature over a period of 1 h. After cooling, 3 μl of 10× ligase-sequenase buffer (4 mM dNTP, 10 mM ATP, 200 mM Tris-HCl, pH 7.5, 40 mM $MgCl_2$, 150 mM DTT) and 5 units each of $T_4$ DNA ligase and Sequenase™ (United States Biochemical, Inc.) were added to the reaction mixture. The mixture was incubated at 25° C. for 5 min and then at 37° C. for 1 h. After the last incubation, 5 μg of yeast RNA and 2½ volumes of ethanol were added and the nucleic acids were precipitated at −70° C. for 1 h. The precipitate was collected by centrifugation in an Eppendorf microfuge for 10 min, dried and resuspended in 17 μl of $dH_2O$. Ligation was continued by adding 2 μl of 10× ligation buffer, 1 unit of ligase and incubating overnight at 15° C.

D. Isolation of DNA fragments: DNA fragments from restriction enzyme digestions or from the ligation reactions were separated on 2% agarose gels in 1×TAE buffer (40 mM Tris-acetate, 2 mM EDTA) containing 0.5 μg/ml ethidium bromide. The bands on the agarose gels corresponding to the expected DNA fragments were identified under long wave length UV illumination.

For DNA fragments equal or greater than 1000 bp, the corresponding band was cut out of the gel and the DNA was extracted by the Gene Clean™ method according to the manufacturer's instructions (Bio 101, Inc.).

For DNA fragments less than 1000 bp, a piece of DE-81 paper was inserted into the agarose gel in front of the identified DNA fragment. Electrophoresis was resumed for several minutes, then the DE-81 paper was removed and soaked in about 200–300 μl fragment elution buffer (20 mM Tris-HCl, pH 7.5, 1 mM EDTA, 1.5M NaCl) at 37° C. for several hours. The mixture filtered through glass wool to remove paper residues. The DNA fragment was precipitated from solution as described at the end of Section 1B (recovery of phosphorylated oligonucleotides) and resuspended in the desired volume of $dH_2O$ or buffer.

E. Polymerase chain reaction (PCR): PCR was used to prepare DNA cassettes and to incorporate partial spacer domains and restriction enzyme sites at the ends of these products.

PCR was conducted with 2 μg DNA template, 1.25 mM each NTP, 8 μg each of the sense and antisense primer and 2.5 units of Taq polymerase in 100 μl of PCR buffer (50 mM KCl, 10 mM Tris-HCl, p H 8.3, 1.5 mM $MgCl_2$, 0.01% (w/v) gelatin). The mixture was covered with 50 μl mineral oil, placed in a DNA Thermal Cycler (Perkin Elmer Cetus Corp.) and heat denatured at 92° C. for 3 min. PCR was then consisted of 5 cycles for 1 min at 35° C., 2 min at 70° C. and 1 min at 92° C. followed by 25 cycles for 1 min at 50° C., 2 min at 70° C. and 1 min at 92° C. The PCR products were electrophoresed in a 2% agarose gel and isolated as described above.

EXAMPLE 2

Construction of Synthetic MEAV Gene

The synthetic MEAV gene was assembled from DNA cassettes encoding a portion of the HIV $CD_4$ binding site and various HIV epitopes. The MEAV gene encodes alternating peptide and spacer domains and is shown schematically in FIG. 1. The peptide domains are a portion of the CD4 binding site from HIV gp120 (region A), and different $V_3$ loop epitopes from five seroprevalent HIV-1 variants (denoted as regions MN, SC, RF, IIIB and WMJ2). Each peptide domain is followed by a spacer domain composed of the amino acid sequence PPDPDP, a sequence adapted from an immunoglobulin heavy chain hinge region. FIG. 2 shows the complete nucleotide and amino acid sequence of the MEAV gene. The nucleotide sequence for MEAV was designed for optimal codon usage in E. coli. Each peptide domain (A, MN, SC, RF, IIIB and WMJ2) is indicated in FIG. 2.

For assembling the MEAV gene, subclones encoding each of the six peptide domains were constructed by inserting synthetic oligonucleotides into the BamHI and HindIII sites of pUC18. The various subclones were assembled as described below from the oligonucleotides listed in Table 2.

Subclone pUC-A was constructed by annealing the partially complementary oligonucleotides A+ (annealed at the BamHI site) and A– (annealed at the HindIII site) with BamHI- and HindIII-digested vector and filling the resultant gap by polymerase extension before ligation. In addition, the A region subclone has a HpaI site adjacent to the BamHI to facilitate further cloning and a PstI site six nucleotides upstream from the coding region for use in construction of the expression vector.

Subclones pUC-MN, pUC-SC, pUC-RF and pUC-WMJ2 were constructed by annealing two pairs of complementary, and partially overlapping oligonucleotides with BamHI- and HindIII-digested vector followed by ligation. The +1 oligonucleotide of each group annealed at the BamHI site of the vector and was complementary to the −1 oligonucleotide. The +2 oligonucleotide then annealed to complementary sequences at the 5' end of the −1 oligonucleotide. The +2 oligonucleotide was complementary to the −2 oligonucleotide which annealed at the HindIII site of the vector.

Subclone pUC-IIIB was constructed by annealing complementary oligonucleotides IIIB+ (anneals at the BamHI site) and IIIB– (anneals at the HindIII site) with BamHI– and HindIII-digested vector followed by ligation.

Figure 4:
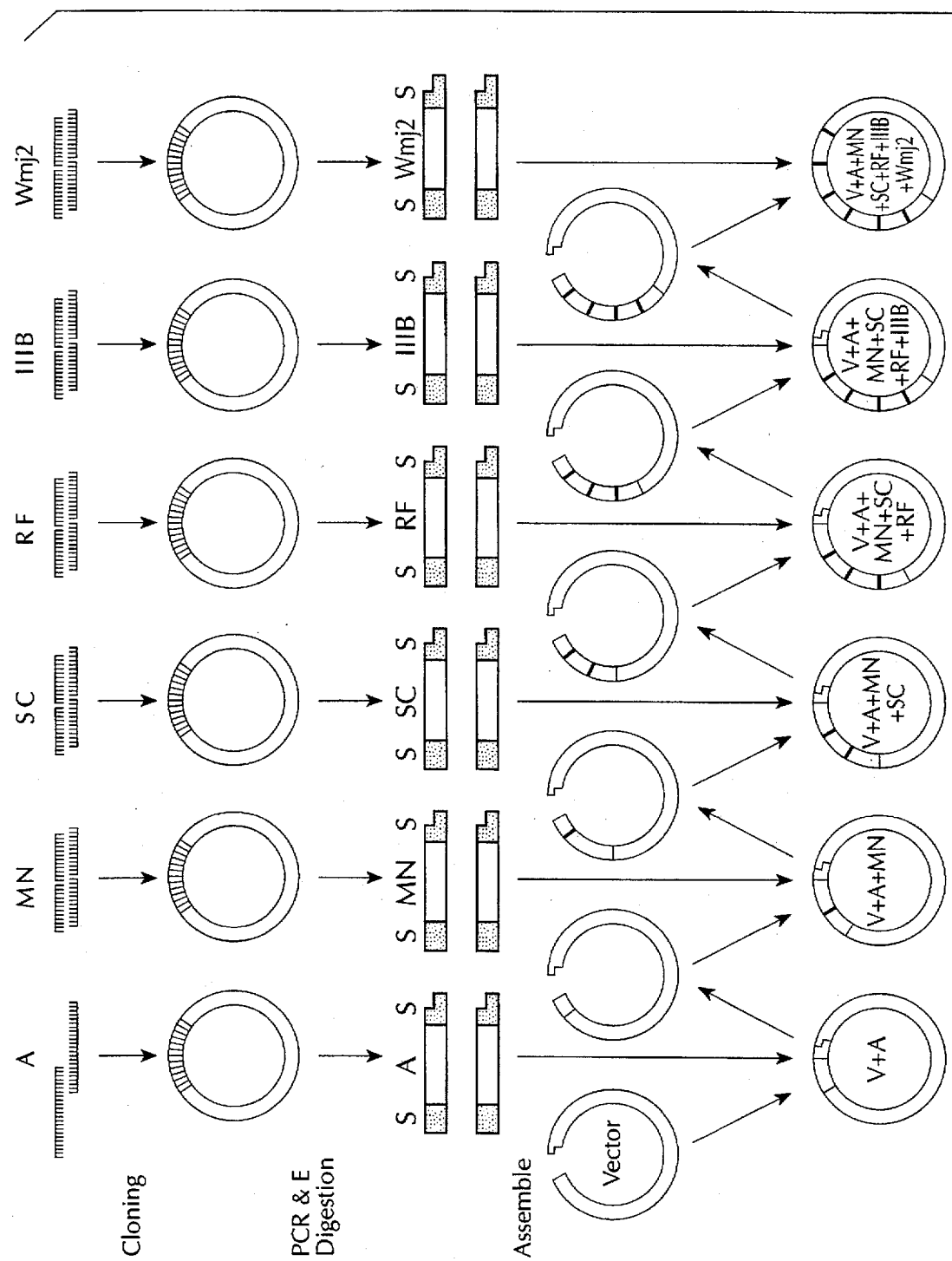
FIG. 4 illustrates the cassette assembly scheme used in construction of the synthetic MEAV gene. Cloning: Oligonucleotides encoding each peptide domain were synthesized and inserted into the BamHI and HindIII cloining sites of the vector pUC18. Open boxes represent pUC18 and the diagonal-filled box represents the peptide domain. PCR & E digestion: The individual peptide domains were amplified by PCR. Partial spacer sequences (at the 5' and 3' ends) and NaeI and HindIII sites (at the extreme 3' end) were added to each peptide domain during PCR amplification. The open boxes represent the peptide domain and the solid boxes (marked S) represent the partial spacer and restriction enzyme sequences. After amplification, the fragments were digested with HindIII. Assemble: The amplified A domain was inserted into pUC18 at the HpaI and HindIII sites to generate the V+A vector depicted in the lower left corner. The V+A vector was digested with NaeI and HindIII and the amplified MN fragment was inserted to create the complete spacer domain between A and MN and thereby generate the V+A+MN vector. Each successive domain is added in a similar manner to produce the vector depicted in the lower right corner. See Example 2 for the details on completion of the final spacer domain following the WMJ2 peptide domain and production of pMEAV.

After construction of each subclone, PCR was used to amplify a DNA fragment containing partial spacer domains and the coding region of each peptide domain using the strategy and primers shown in FIG. 3. The MEAV gene was then assembled as shown in FIG. 4.

The PCR primer added the sequence CCGCCG-GCAAGCTT (SEQ ID NO:59) to the 3' end of the peptide domain (encoding PP of the spacer, the NaeI and HindIII sites). With the exception of the A domain, the PCR primer added the sequence AGATCCGGATCCG (SEQ ID NO:60) to the 5' end of each peptide domain (encoding DPDP of the spacer). The 5' end of the A domain was amplified from the AAC of the HpaI site without incorporation of additional nucleotides.

To assemble the synthetic MEAV gene, each of the amplified fragments were digested with HindIII and purified. The amplified A domain was inserted into pUC18 at the HpaI and HindIII sites to produce the V+A vector depicted in the lower left corner of FIG. 4. The V+A vector was then digested with NaeI and HindIII and the amplified MN fragment was inserted to create the spacer domain between A and MN and thereby produce the V+A+MN vector. Each successive domain was added in a similar manner to produce the V+A+MN+SC+RF+IIIB+WMJ2 vector. To complete the final spacer domain and provide three stop codons, the latter vector was digested with NaeI and HindIII two complementary oligonucleotides (Stop+ and Stop–; Table 2) encoding these sequences were inserted to produce pMEAV.

TABLE 2

Sequence of the oligonucleotides used to construct MEAV peptide domain subclones A+ (65 mer; SEQ ID NO:36)
5'-GATCCGTTAA CGGCTGCAGA ATCAAACAGG TCATCAACAT GTGGCAGGAA GTTGGTAAAG CTATG
A– (66 mer; SEQ ID NO:37)
5'-AGCTTAAATG ATCACAACGG ATCTGACCAG AGATCGGCGG AGCGTACATA GCTWTACCAA CTTCCT
MN+1 (31 mer; SEQ ID NO:38)
5'-GATCCTTTAA ACGTATCCAC ATCGGTCCGG G
MN+2 (31 mer; SEQ ID NO:39)
5'-TCGTGCTTTC GTTACCACCA AAAACCCGGG A
MN–1 (31 mer; SEQ ID NO:40)
5'-ACGACCCGGA CCGAIGTGGA TACGTTTAAA G
MN–2 (31 mer; SEQ ID NO:41)
5'-AGCTTCCCGG GTTTTTGGTG GTAACGAAAG C
SC+1 (31 mer; SEQ ID NO:42)
5'-GATCCATCGA TCTATCCACA TCGGTCCGGG T
SC+2 (29 mer; SEQ ID NO:43)
5'-CGTGCTTTCG TTGCTACCGG TGATATCAA
SC–1 (32 mer; SEQ ID NO:44)
5'-GCACGACCCG GACCGATGTG GATAGATCGA TG
SC–2 (28 mer; SEQ ID NO:45)
5'-AGCTTTGATA TCACCGGTAG CAACGAAA
RF+1 (34 mer; SEQ ID NO:46)
5'-GATCCTTTAA ATCTATCCGT ATCACCAAAG GTCC
RF+2 (34 mer; SEQ ID NO:47)

TABLE 2-continued

Sequence of the oligonucleotides used to construct
MEAV peptide domain subclones 5'-GGGTCGTGTT ATCGTTGCTA CCGGTCAAGA TCTA
RF-1 (34 mer; SEQ ID NO:48)
5'-ACCCGGACCT TTGGTGATAC GGATAGATTT AAAG
RF - 2 (34 mer; SEQ ID NO:49)
5'-AGCTTAGATC TTGACCGGTA GCAACGATAA CACG
IIIB+ (62 mer; SEQ ID NO:50)
5'-GATCCTTTAA ATCTATCCGT ATCCAGCGTG GTCCGGGTCG TGCTTTCGTT
ACCATCGGTA AA
IIIB- (62 mer; SEQ ID NO:51)
5'-AGCTTTTACC GATGGTAACG AAAGCACGAC CCGGACCACG CTGGATACGG
ATAGATTTAA AG
WMJ2+1 (31 mer; SEQ ID NO:52)
5'-GATCCATCGA TCTCTGTCTA TCGGTCCGGG T
WMJ2+2 (27 mer; SEQ ID NO:53)
5'-CGTGCTTTCC GTACCCGTGA AGATCTA
WMJ2-1 (32 mer; SEQ ID NO:54)
5'-GCACGACCCG GACCGATAGA CAGAGATCGA TG
WMJ2-2 (26 mer; SEQ ID NO:55)
5'-AGCTTAGATC TTCACGGGTA CGGAAA
Stop+ (28 mer; SEQ ID NO:56)
5'-AGACCCGGAC CCGGAAGAAT AGTGATAA
Stop- (32 mer; SEQ ID NO:57)
5'-AGCTTTATCA CTATTCTTCC GGGTCCGGGT CT

EXAMPLE 3

Expression of MEAV Gene

The expression vector pKK-MEAV was constructed by isolating the PstI-HindIII fragment from pMEAV containing the MEAV gene and ligating it into the expression vector pKK233-2 (Pharmacia LKB Biotechnology) which had been similarly digested. The pKK-MEAV vector was transformed into *E. coli* strain BL21 and tested for expression of MEAV by IPTG induction as described by Brosius et al. (1984) Proc. Natl. Acad. Sci. USA 81:6929.

Figure 6A:
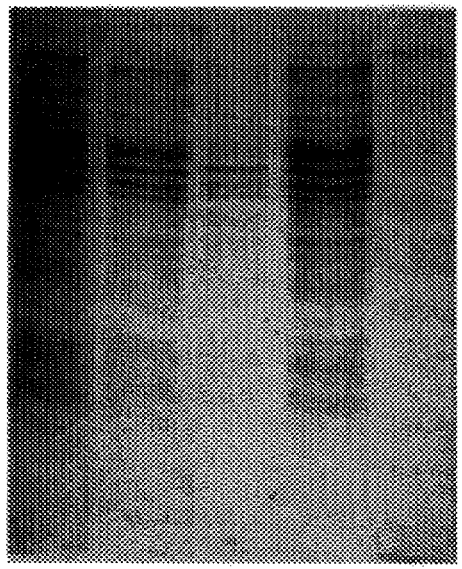
FIG. 6 depicts the expression of the MEAV protein obtained in *E. coli* strain BL21 on (A) a Coomassie blue-stained gel and (B) a Western Blot probed with a mixture of polyclonal antibodies against the MN and IIIB regions. The lanes contain (1) a whole cell lysate of *E. coli* strain BL21, (2) a whole cell lysate of *E. coli* strain BL21 containing plasmid pKK-233, (3) a whole cell lysate of *E. coli* strain BL21 containing plasmid pKK-MEAV before IPTG induction and (4) a whole cell lysate of *E. coli* strain BL21 containing plasmid pKK-MEAV after IPTG induction.

The cells from 1 ml of the bacterial culture were isolated, suspended in 50 µl of lysate buffer (2% SDS, 1% Beta-mercaptoethanol, 10 mM EDTA) and boiled for 10 min. The lysate was mixed with an equal volume of 2× loading buffer (125 mM Tris, pH 6.8, 2% SDS, 20% glycerol, 0.001% bromphenol blue), boiled for 5 min and analyzed by SDS-polyacrylamide gel electrophoresis (PAGE). The results in FIG. 6(A) show the expression of the MEAV protein obtained in *E. coli* strain BL21 on a Coomassie blue-stained gel. The lanes contain (1) a whole cell lysate of *E. coli* strain BL21, (2) a whole cell lysate of *E. coli* strain BL21 containing plasmid pKK-233, (3) a whole cell lysate of *E. coli* strain BL21 containing plasmid pKK-MEAV before IPTG induction, (4) a whole cell lysate of *E. coli* strain BL21 containing plasmid pKK-MEAV after IPTG induction and (M) molecular weight standards. A band corresponding to the MEAV protein could not be identified in the whole cell lysates by lysates by coomassie blue stain.

Figure 6B:
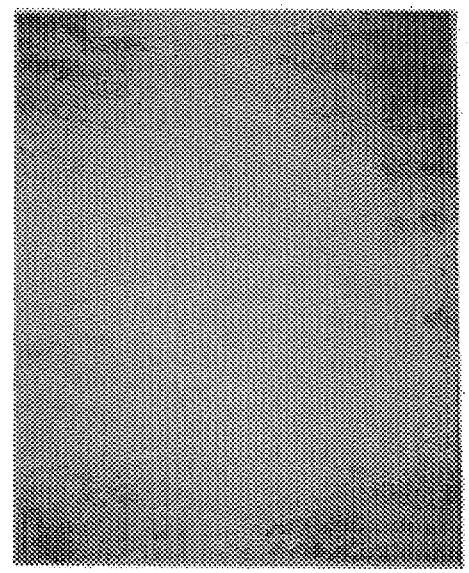

To show that MEAV was expressed, a Western blot analysis was done on the whole cell lysates prepared as described above. After electrophoresis, the proteins were transferred to nitrocellulose and reacted with a mixture of guinea pig polyclonal antibodies directed against peptides from the MN and IIIB regions (see Example 5 for the sequences) using 1:1000 serum dilution according to the method described in Unit 10.8 of Innis et al. Goat anti-guinea pig IgG conjugated to horseradish peroxidase was used as the second antibody. The results shown in FIG. 6(B) indicate that MEAV is produced in strain BL21 after IPTG induction. The lanes of FIG. 6B are the same as in FIG. 6(A).

EXAMPLE 4

Purification of Recombinant MEAV

Two ml of an overnight culture of BL21/pKK-MEAV was transferred to 100 ml LB medium and incubated at 37° C. with vigorous shaking for about 4 h. When the culture reached an $OD_{600}$ of 0.6 to 0.7, IPTG was added to final a concentration of 0.4 mM. The culture was further incubated at 37° C. for 2 h and the cells collected by centrifugation at 7500 rpm (Sorvall SS-34 rotor) for 10 min. The cell pellet was washed three times with 25 ml of TE (10 mM Tris, 1 mM EDTA, pH 7.4) and collected by centrifugation as above.

The washed pellet was resuspended in 5 ml of Buffer I (10 mM Tris-HCl, pH 8.0, 0.25M sucrose, 1 mM EDTA), transferred to a Parr bomb, and pressurized at 1500 psi for 20 min under nitrogen. The cells were then lysed by rapid reduction to atmospheric pressure. The pellet, containing MEAV in inclusion bodies, was collected by centrifugation at 12,000 rpm (Sorvall SS-34 rotor) for 10 min and resuspended in 2 ml of Buffer I.

Inclusion bodies were isolated by overlaying the above solution on a sucrose step gradient consisting of 3 ml each of 60%, 50% and 40% (w/w) sucrose in buffer I and centrifuging at 108,000×g for 2 h. The inclusion bodies which were located at the 50–60% sucrose interface were removed and washed 3 time in $dH_2O$. The pellet in each wash was collected by centrifugation at 10,000 rpm (Sorvall SS-34 rotor) for 10 min.

After the final wash, the inclusion bodies were resuspended in 5 ml of 20 mM Tris-Cl (pH 8.0), 10 mM EDTA and 7M guanidinium hydrochloride (GdmHCl). The suspension was adjusted to pH 8.5 with 2N NaOH containing 7M GdmHCl and incubated at room temperature for about 6 h until the inclusion bodies had dissolved.

The dissolved inclusion bodies were loaded on a Sephadex™ G-25 column (45×1.5 cm), equilibrated in phosphate-buffered saline (PBS). The column was eluted with PBS and protein elution was monitored at $OD_{280}$. The first protein peak was pooled, concentrated by polyethylene glycol dehydration and loaded on a Sephadex G-200 column (45×2.0 cm) equilibrated in PBS. The column was eluted with PBS and protein monitored at $OD_{280}$. The single peak of protein was pooled and concentrated to 250 µg/ml by polyethylene dehydration.

EXAMPLE 5

Guinea Pig Immunization and Response to MEAV

The immunoreactivity of MEAV and its ability to elicit neutralizing antibodies was determined. Antibodies against MEAV were raised by injecting crude recombinant protein prepared as in Example 4 into a guinea pig. The guinea pig was pre-bled and first injected subcutaneously (s.c.) with 100 µg protein (in 0.4 ml) emulsified with an equal volume of Freunds' complete adjuvant. The subsequent injections at 3 and 6 weeks consisted of 100 µg protein emulsified in Freunds' incomplete adjuvant administered s.c. Blood (1 ml) was collected every three weeks after the first injection. Each sample was analyzed against a panel of peptides using a standard EIA format as described in Hosein et al. (1991) Proc. Natl. Acad. Sci. USA. 88:3642–3651. For the EIA, the microtiter wells were coated overnight with 100 µl of 5 µg/ml peptide using the following peptides:

A: CRIKQIINMWQEVGKAMYAPPISGQIRC-octamer

MN: ESVQINCTRPNYNKRKRIHIGPGRAFYTTKN-octamer

SC: EAVEINCTRPNNNTTRSIHIGPGRAFYATGD-octamer

RF: ASVQINCTRPNNNTRKSITKGPGRVIYATGQ-octamer

IIIB: QSVEINCTRPNNNTRKSIRIQRGPGRAFV-TIGK-octamer

WMJ2: ESVEINCTRPYNNVRRSLSIGPGRAFRTRE-octamer (The octamer consists of a heptalysine core).

Figure 7:
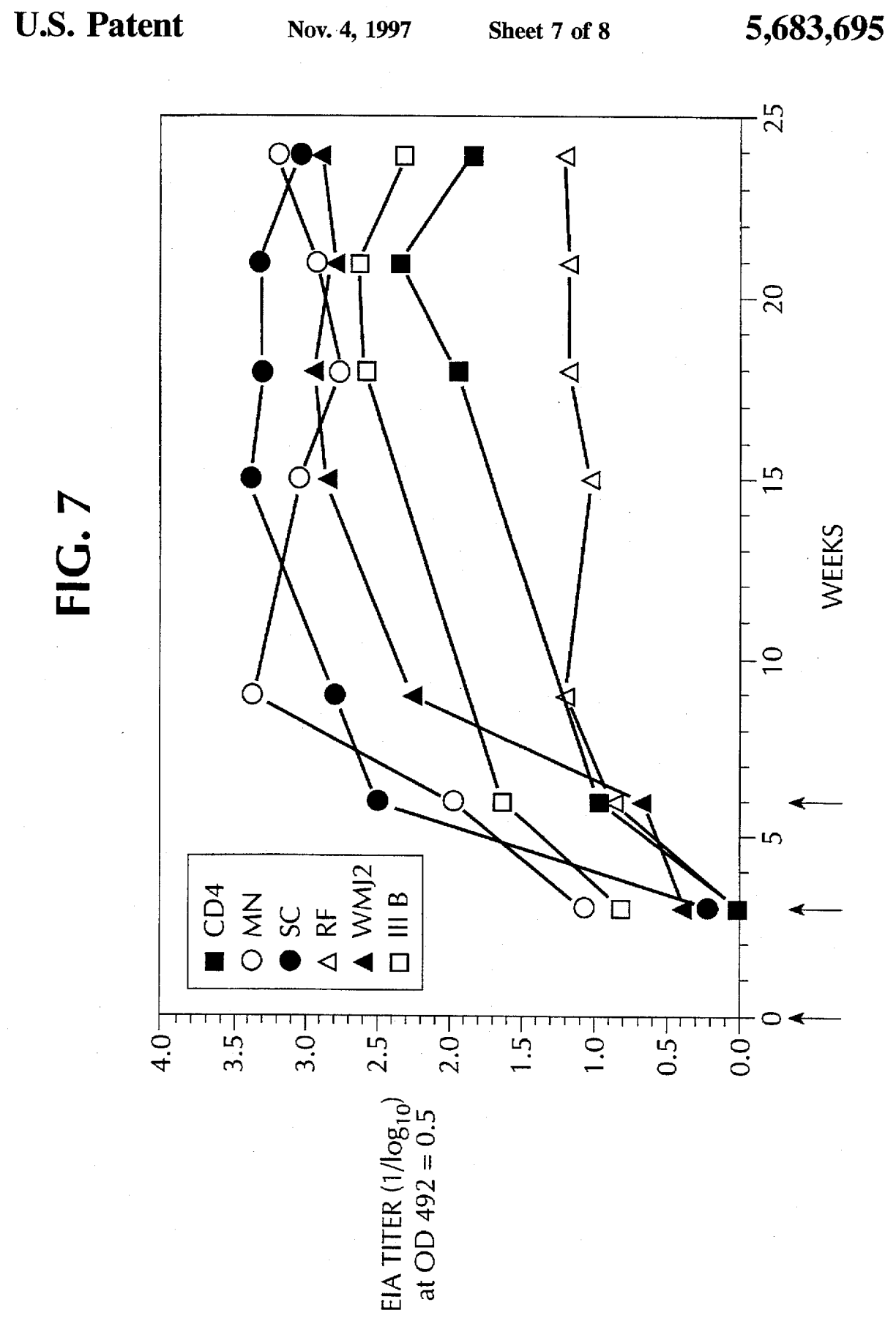

The results shown in FIG. 7 indicate the titer of serum which gave a positive signal of 0.5 $OD_{492}$ for the IIIB (open square), MN (open circle), SC (solid circle), $CD_4$ (solid square), RF (open triangle), or WMJ2 (solid triangle) peptides.

Figure 8:
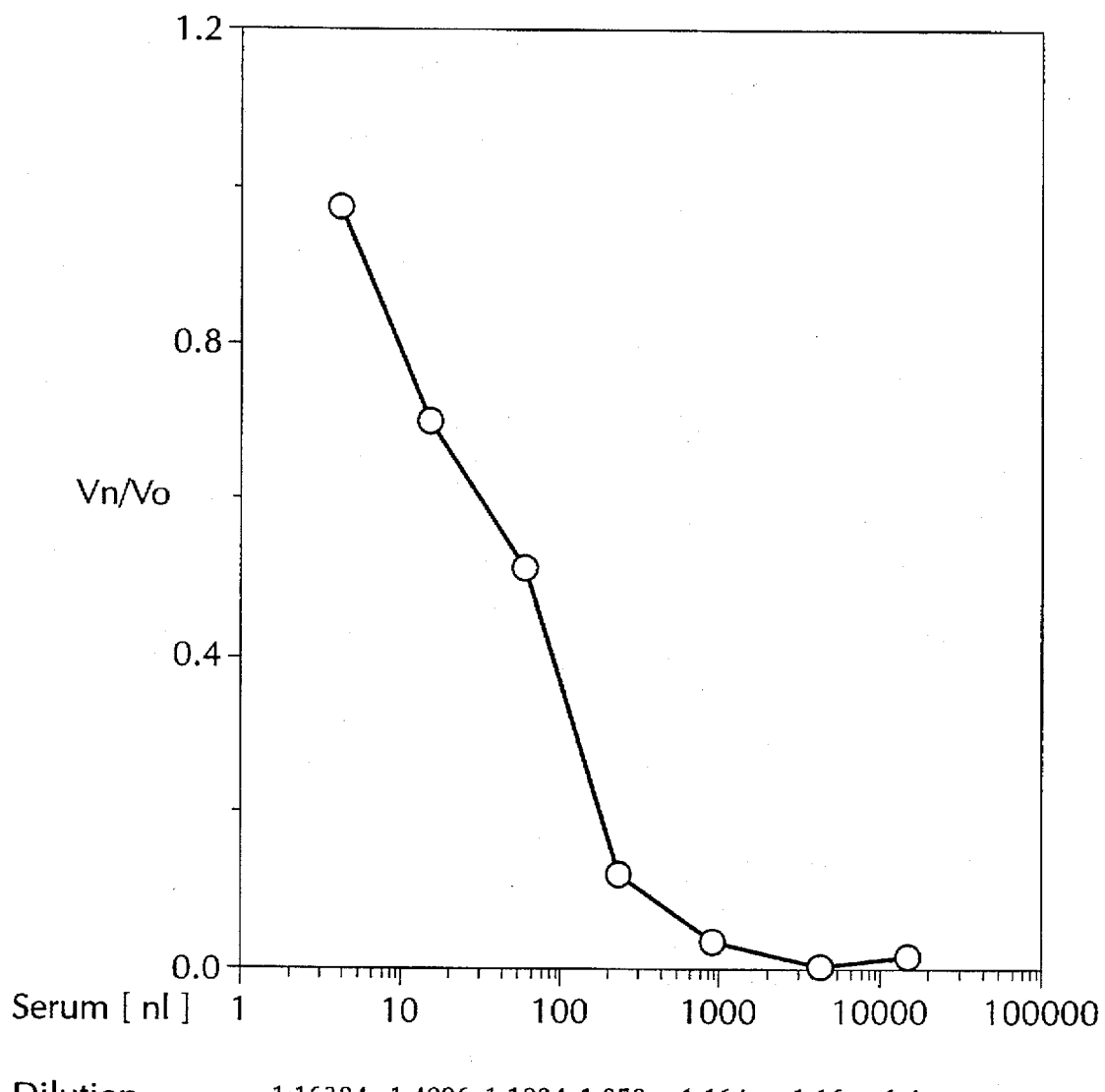
FIG. 8 depicts a titration curve showing the neutralization of HIV-1 MN on CD4 gene-transfected HeLa cells by anti-MEAV serum raised in guinea pigs.

Neutralizing antibody (NA) titers for HIV-$1_{MN}$ were determined by the syncytium inhibition NA assay. Briefly, neutralization of 200 syncytia forming units (SFU) of HIV-$1_{MN}$ were measured with serially diluted guinea pig anti-MEAV antisera ranging from 1:4 to 1:16,384 and expressed as surviving fraction of input virus ($V_n/V_o$). Virus and sera mixtures, preincubated for 45 min at 4° C. and 15 min at 20° C., were incubated for 2 h with HT4-6 Hela CD4+ cells (pretreated with DEAE-dextran) seeded 24 h previously into 48-well plates at a density of $4\times10^4$ cells/well. Neutralization plates were incubated for 5 days, fixed in methanol, stained and scored. Representative results are shown in FIG. 8. The serum displayed neutralization activity for HIV-$1_{MN}$ at a level of 1:1024 dilution for 50% survival. The serum neutralization activity is evidence for the ability of MEAV to induce a broadly protective immune response in immunized animals.

We claim:

1. A recombinant protein which comprises alternating peptide and spacer domains wherein said protein has an amino acid sequence which comprises SEQ ID NO:8.

2. An isolated nucleic acid encoding a recombinant protein which comprises alternating peptide and spacer domains wherein said protein has an amino acid sequence which comprises SEQ ID NO:8.

* * * * *

SEQUENCE LISTING ( 1 ) GENERAL INFORMATION:

( i i i ) NUMBER OF SEQUENCES: 73

( 2 ) INFORMATION FOR SEQ ID NO:1:

( i ) SEQUENCE CHARACTERISTICS:
( A ) LENGTH: 17 amino acids
( B ) TYPE: amino acid
( D ) TOPOLOGY: linear ( i i ) MOLECULE TYPE: peptide ( x i ) SEQUENCE DESCRIPTION: SEQ ID NO:1:

Lys Ala Ile His Ile Gly Pro Gly Arg Ala Phe Val Thr Thr Lys Asn
1               5                   10                  15

Pro ( 2 ) INFORMATION FOR SEQ ID NO:2:

( i ) SEQUENCE CHARACTERISTICS:
( A ) LENGTH: 16 amino acids
( B ) TYPE: amino acid
( D ) TOPOLOGY: linear ( i i ) MOLECULE TYPE: peptide ( x i ) SEQUENCE DESCRIPTION: SEQ ID NO:2:

Arg Ser Ile His Ile Gly Pro Gly Arg Ala Phe Val Ala Thr Gly Asp
1               5                   10                  15

( 2 ) INFORMATION FOR SEQ ID NO:3:

( i ) SEQUENCE CHARACTERISTICS:
    ( A ) LENGTH: 18 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:3:

```
Lys Ser Ile Arg Ile Thr Lys Gly Pro Gly Arg Val Ile Val Ala Thr
1               5                   10                  15
Gly Gln
```

( 2 ) INFORMATION FOR SEQ ID NO:4:

( i ) SEQUENCE CHARACTERISTICS:
    ( A ) LENGTH: 18 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:4:

```
Lys Ser Ile Arg Ile Gln Arg Gly Pro Gly Arg Ala Phe Val Thr Ile
1               5                   10                  15
Gly Lys
```

( 2 ) INFORMATION FOR SEQ ID NO:5:

( i ) SEQUENCE CHARACTERISTICS:
    ( A ) LENGTH: 15 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:5:

```
Arg Ser Leu Ser Ile Gly Pro Gly Arg Ala Phe Arg Thr Arg Glu
1               5                   10                  15
```

( 2 ) INFORMATION FOR SEQ ID NO:6:

( i ) SEQUENCE CHARACTERISTICS:
    ( A ) LENGTH: 29 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:6:

```
Cys Arg Ile Lys Gln Val Ile Met Met Trp Gln Glu Val Gly Lys Ala
1               5                   10                  15
Met Tyr Ala Pro Pro Ile Ser Gly Gln Ile Arg Cys Asp
                20                  25
```

( 2 ) INFORMATION FOR SEQ ID NO:7:

( i ) SEQUENCE CHARACTERISTICS:
    ( A ) LENGTH: 6 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:7:

```
Pro Pro Xaa Pro Xaa Pro
1               5
```

( 2 ) INFORMATION FOR SEQ ID NO:8:

( i ) SEQUENCE CHARACTERISTICS:
        ( A ) LENGTH: 150 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:8:

```
Cys Arg Ile Lys Gln Val Ile Met Met Trp Gln Glu Val Gly Lys Ala
  1               5                  10                  15
Met Tyr Ala Pro Pro Ile Ser Gly Gln Ile Arg Cys Asp Pro Pro Asp
             20                  25                  30
Pro Asp Pro Lys Ala Ile His Ile Gly Pro Gly Arg Ala Phe Val Thr
             35                  40                  45
Thr Lys Asn Pro Pro Asp Pro Asp Pro Arg Ser Ile His Ile Gly Pro
         50              55                  60
Gly Arg Ala Phe Val Ala Thr Gly Asp Pro Pro Asp Pro Asp Pro Lys
 65              70                  75                  80
Ser Ile Arg Ile Thr Lys Gly Pro Gly Arg Val Ile Val Ala Thr Gly
                 85                  90                  95
Gln Pro Pro Asp Pro Asp Pro Lys Ser Ile Arg Ile Gln Arg Gly Pro
             100                 105                 110
Gly Arg Ala Phe Val Thr Ile Gly Lys Pro Pro Asp Pro Asp Pro Arg
         115                 120                 125
Ser Leu Ser Ile Gly Pro Gly Arg Ala Phe Arg Thr Arg Glu Pro Pro
         130                 135                 140
Asp Pro Asp Pro Glu Glu
         145                 150
```

( 2 ) INFORMATION FOR SEQ ID NO:9:

( i ) SEQUENCE CHARACTERISTICS:
        ( A ) LENGTH: 32 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:9:

```
Glu Ser Val Glu Ile Asn Cys Thr Arg Pro Asn Asn Asn Thr Arg Lys
  1               5                  10                  15
Ser Ile His Ile Gly Pro Gly Arg Ala Phe Tyr Thr Thr Gly Glu Met
             20                  25                  30
```

( 2 ) INFORMATION FOR SEQ ID NO:10:

( i ) SEQUENCE CHARACTERISTICS:
        ( A ) LENGTH: 32 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:10:

```
Glu Ser Val Glu Ile Asn Cys Thr Arg Pro Asn Asn Asn Thr Arg Lys
  1               5                  10                  15
Ser Ile His Ile Gly Pro Gly Gln Ala Phe Tyr Ala Thr Gly Asp Met
             20                  25                  30
```

( 2 ) INFORMATION FOR SEQ ID NO:11:

(i) SEQUENCE CHARACTERISTICS:
  (A) LENGTH: 32 amino acids
  (B) TYPE: amino acid
  (D) TOPOLOGY: linear (ii) MOLECULE TYPE: peptide (xi) SEQUENCE DESCRIPTION: SEQ ID NO:11:

```
Lys Pro Val Arg Ile Asn Cys Thr Arg Pro Asn Asn Asn Thr Arg Lys
1               5                  10                 15
Ser Val His Ile Gly Pro Gly Gln Thr Phe Tyr Ala Thr Gly Asp Met
            20                  25                 30
```

(2) INFORMATION FOR SEQ ID NO:12:

(i) SEQUENCE CHARACTERISTICS:
    (A) LENGTH: 32 amino acids
    (B) TYPE: amino acid
    (D) TOPOLOGY: linear (ii) MOLECULE TYPE: peptide (xi) SEQUENCE DESCRIPTION: SEQ ID NO:12:

```
Glu Ser Val Glu Ile Val Cys Thr Arg Pro Asn Asn Asn Thr Arg Lys
1               5                  10                 15
Ser Ile Arg Ile Gly Pro Gly Gln Thr Phe Tyr Ala Thr Gly Asp Met
            20                  25                 30
```

(2) INFORMATION FOR SEQ ID NO:13:

(i) SEQUENCE CHARACTERISTICS:
    (A) LENGTH: 32 amino acids
    (B) TYPE: amino acid
    (D) TOPOLOGY: linear (ii) MOLECULE TYPE: peptide (xi) SEQUENCE DESCRIPTION: SEQ ID NO:13:

```
Glu Ser Val Thr Ile Asn Cys Thr Arg Pro Tyr Asn Asn Thr Arg Gln
1               5                  10                 15
Arg Thr His Ile Gly Pro Gly Gln Ala Leu Tyr Thr Thr Gly Arg Met
            20                  25                 30
```

(2) INFORMATION FOR SEQ ID NO:14:

(i) SEQUENCE CHARACTERISTICS:
    (A) LENGTH: 32 amino acids
    (B) TYPE: amino acid
    (D) TOPOLOGY: linear (ii) MOLECULE TYPE: peptide (xi) SEQUENCE DESCRIPTION: SEQ ID NO:14:

```
Lys Ser Val Glu Ile Asn Cys Thr Arg Pro Ser Asn Asn Thr Arg Thr
1               5                  10                 15
Ser Ile Thr Ile Gly Pro Gly Gln Val Phe Tyr Arg Thr Gly Asp Met
            20                  25                 30
```

(2) INFORMATION FOR SEQ ID NO:15:

(i) SEQUENCE CHARACTERISTICS:
    (A) LENGTH: 32 amino acids
    (B) TYPE: amino acid
    (D) TOPOLOGY: linear (ii) MOLECULE TYPE: peptide (xi) SEQUENCE DESCRIPTION: SEQ ID NO:15:

```
        Lys Ala Val Lys Ile Asn Cys Thr Arg Pro Asn Lys Thr Thr Arg Lys
        1               5                   10                  15

Gly Val Arg Ile Gly Pro Gly Gln Ala Trp Tyr Ala Arg Gly Asn Met
                        20              25                  30
```

(2) INFORMATION FOR SEQ ID NO:16:

(i) SEQUENCE CHARACTERISTICS:
    (A) LENGTH: 32 amino acids
    (B) TYPE: amino acid
    (D) TOPOLOGY: linear (ii) MOLECULE TYPE: peptide (xi) SEQUENCE DESCRIPTION: SEQ ID NO:16:

```
        Glu Ser Val Gln Ile Asn Cys Thr Arg Pro Asn Tyr Asn Lys Arg Lys
        1               5                   10                  15

Arg Ile His Ile Gly Pro Gly Arg Ala Phe Tyr Thr Thr Lys Asn Met
                        20              25                  30
```

(2) INFORMATION FOR SEQ ID NO:17:

(i) SEQUENCE CHARACTERISTICS:
    (A) LENGTH: 32 amino acids
    (B) TYPE: amino acid
    (D) TOPOLOGY: linear (ii) MOLECULE TYPE: peptide (xi) SEQUENCE DESCRIPTION: SEQ ID NO:17:

```
        Glu Ala Val Glu Ile Asn Cys Thr Arg Pro Asn Asn Asn Thr Thr Arg
        1               5                   10                  15

Ser Ile His Ile Gly Pro Gly Arg Ala Phe Tyr Ala Thr Gly Asp Met
                        20              25                  30
```

(2) INFORMATION FOR SEQ ID NO:18:

(i) SEQUENCE CHARACTERISTICS:
    (A) LENGTH: 32 amino acids
    (B) TYPE: amino acid
    (D) TOPOLOGY: linear (ii) MOLECULE TYPE: peptide (xi) SEQUENCE DESCRIPTION: SEQ ID NO:18:

```
        Glu Ser Val Glu Ile Asn Cys Thr Arg Pro Asn Asn Asn Thr Arg Lys
        1               5                   10                  15

Ser Ile His Met Gly Pro Gly Ser Ala Phe Tyr Ala Thr Gly Asp Met
                        20              25                  30
```

(2) INFORMATION FOR SEQ ID NO:19:

(i) SEQUENCE CHARACTERISTICS:
    (A) LENGTH: 32 amino acids
    (B) TYPE: amino acid
    (D) TOPOLOGY: linear (ii) MOLECULE TYPE: peptide (xi) SEQUENCE DESCRIPTION: SEQ ID NO:19:

```
        Glu Thr Val Lys Ile Asn Cys Ala Arg Leu Asn Asn Thr Arg Arg
        1               5                   10                  15

Ser Ile Pro Val Gly Pro Gly Lys Ala Leu Tyr Thr Thr Gly Asp Met
                        20              25                  30
```

( 2 ) INFORMATION FOR SEQ ID NO:20:

( i ) SEQUENCE CHARACTERISTICS:
        ( A ) LENGTH: 32 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:20:

```
Gln  Ser  Val  Glu  Ile  Val  Tyr  Thr  Arg  Pro  Asn  Asn  Asn  Thr  Arg  Lys
1                   5                        10                       15

Gly  Val  Arg  Ile  Gly  Pro  Gly  Gln  Thr  Phe  Tyr  Ala  Thr  Gly  Asp  Met
              20                       25                       30
```

( 2 ) INFORMATION FOR SEQ ID NO:21:

( i ) SEQUENCE CHARACTERISTICS:
        ( A ) LENGTH: 32 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:21:

```
Lys  Ser  Ile  Ala  Ile  Thr  Cys  Thr  Arg  Pro  Tyr  Asn  Asn  Thr  Arg  Gln
1                   5                        10                       15

Arg  Thr  Arg  Ile  Gly  Ser  Gly  Gln  Ala  Phe  Tyr  Thr  Thr  Gly  Arg  Met
              20                       25                       30
```

( 2 ) INFORMATION FOR SEQ ID NO:22:

( i ) SEQUENCE CHARACTERISTICS:
        ( A ) LENGTH: 32 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:22:

```
Lys  Ser  Val  Glu  Ile  Asn  Cys  Thr  Arg  Pro  Ser  Asn  Asn  Thr  Arg  Thr
1                   5                        10                       15

Ser  Ile  Pro  Ile  Gly  Pro  Gly  Gln  Val  Phe  Tyr  Arg  Thr  Gly  Asp  Met
              20                       25                       30
```

( 2 ) INFORMATION FOR SEQ ID NO:23:

( i ) SEQUENCE CHARACTERISTICS:
        ( A ) LENGTH: 32 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:23:

```
Glu  Ser  Val  Glu  Ile  Asn  Cys  Thr  Arg  Pro  Asn  Asn  Asn  Thr  Arg  Lys
1                   5                        10                       15

Ser  Ile  His  Leu  Gly  Pro  Gly  Gln  Ala  Trp  Tyr  Thr  Thr  Gly  Gln  Met
              20                       25                       30
```

( 2 ) INFORMATION FOR SEQ ID NO:24:

( i ) SEQUENCE CHARACTERISTICS:
        ( A ) LENGTH: 32 amino acids
        ( B ) TYPE: amino acid
        ( D ) TOPOLOGY: linear ( i i ) MOLECULE TYPE: peptide (x i) SEQUENCE DESCRIPTION: SEQ ID NO:24:

Glu Thr Val Glu Ile Asn Cys Thr Arg Pro Ser Asn Asn Thr Arg Lys
1               5                   10                  15

Ser Ile His Leu Gly Trp Gly Arg Ala Phe Tyr Ala Thr Gly Glu Met
            20                  25                  30

(2) INFORMATION FOR SEQ ID NO:25:

(i) SEQUENCE CHARACTERISTICS:
    (A) LENGTH: 32 amino acids
    (B) TYPE: amino acid
    (D) TOPOLOGY: linear (i i) MOLECULE TYPE: peptide (x i) SEQUENCE DESCRIPTION: SEQ ID NO:25:

Glu Ser Val Glu Ile Asn Cys Thr Arg Pro Ser Asn Asn Thr Arg Lys
1               5                   10                  15

Ser Ile His Met Gly Trp Gly Arg Ala Phe Tyr Thr Thr Gly Ala Met
            20                  25                  30

(2) INFORMATION FOR SEQ ID NO:26:

(i) SEQUENCE CHARACTERISTICS:
    (A) LENGTH: 31 amino acids
    (B) TYPE: amino acid
    (D) TOPOLOGY: linear (i i) MOLECULE TYPE: peptide (x i) SEQUENCE DESCRIPTION: SEQ ID NO:26:

Glu Ser Val Glu Ile Asn Cys Thr Arg Pro Tyr Asn Asn Val Arg Arg
1               5                   10                  15

Ser Leu Ser Ile Gly Pro Gly Arg Ala Phe Arg Thr Arg Glu Met
            20                  25                  30

(2) INFORMATION FOR SEQ ID NO:27:

(i) SEQUENCE CHARACTERISTICS:
    (A) LENGTH: 32 amino acids
    (B) TYPE: amino acid
    (D) TOPOLOGY: linear (i i) MOLECULE TYPE: peptide (x i) SEQUENCE DESCRIPTION: SEQ ID NO:27:

Glu Ser Val Lys Ile Thr Cys Ala Arg Pro Tyr Gln Asn Thr Arg Gln
1               5                   10                  15

Arg Thr Pro Ile Gly Leu Gly Gln Ser Leu Tyr Thr Thr Arg Ser Met
            20                  25                  30

(2) INFORMATION FOR SEQ ID NO:28:

(i) SEQUENCE CHARACTERISTICS:
    (A) LENGTH: 32 amino acids
    (B) TYPE: amino acid
    (D) TOPOLOGY: linear (i i) MOLECULE TYPE: peptide (x i) SEQUENCE DESCRIPTION: SEQ ID NO:28:

Glu Ser Val Val Ile Asn Cys Thr Arg Pro Asn Asn Asn Thr Arg Lys
1               5                   10                  15

Ser Ile Asn Ile Gly Pro Gly Arg Ala Leu Tyr Thr Thr Gly Glu Met
            20                  25                  30

( 2 ) INFORMATION FOR SEQ ID NO:29:

( i ) SEQUENCE CHARACTERISTICS:
        ( A ) LENGTH: 32 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:29:

```
Lys  Ser  Val  Glu  Ile  Asn  Cys  Thr  Arg  Pro  Asn  Asn  Asn  Thr  Lys  Lys
 1                    5                         10                        15
Gly  Ile  Ala  Ile  Gly  Pro  Gly  Arg  Thr  Leu  Tyr  Ala  Arg  Glu  Lys  Met
               20                        25                        30
```

( 2 ) INFORMATION FOR SEQ ID NO:30:

( i ) SEQUENCE CHARACTERISTICS:
        ( A ) LENGTH: 32 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:30:

```
Asp  Pro  Val  Asn  Ile  Thr  Cys  Thr  Arg  Pro  Ser  Asn  Asn  Thr  Arg  Lys
 1                    5                         10                        15
Ser  Ile  His  Ile  Ala  Pro  Gly  Arg  Val  Phe  His  Ala  Thr  Gly  Glu  Met
               20                        25                        30
```

( 2 ) INFORMATION FOR SEQ ID NO:31:

( i ) SEQUENCE CHARACTERISTICS:
        ( A ) LENGTH: 31 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:31:

```
Glu  Thr  Val  Thr  Ile  Asn  Cys  Thr  Arg  Pro  Gly  Asn  Asn  Thr  Arg  Arg
 1                    5                         10                        15
Gly  Ile  His  Phe  Gly  Pro  Gly  Gln  Ala  Leu  Tyr  Thr  Thr  Gly  Met
               20                        25                        30
```

( 2 ) INFORMATION FOR SEQ ID NO:32:

( i ) SEQUENCE CHARACTERISTICS:
        ( A ) LENGTH: 32 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:32:

```
Lys  Pro  Val  Arg  Ile  Asn  Cys  Thr  Arg  Pro  Asn  Asn  Asn  Thr  Arg  Glu
 1                    5                         10                        15
Gly  Val  Gly  Ile  Gly  Pro  Gly  Gln  Thr  Phe  Tyr  Lys  Thr  Gly  Asn  Met
               20                        25                        30
```

( 2 ) INFORMATION FOR SEQ ID NO:33:

( i ) SEQUENCE CHARACTERISTICS:
        ( A ) LENGTH: 32 amino acids
        ( B ) TYPE: amino acid
        ( D ) TOPOLOGY: linear (ii) MOLECULE TYPE: peptide (xi) SEQUENCE DESCRIPTION: SEQ ID NO:33:

```
Glu  Ser  Val  Thr  Ile  Asn  Cys  Thr  Arg  Pro  Tyr  Ser  Asn  Thr  Arg  Gln
1                   5                        10                       15

Gly  Thr  His  Ile  Gly  Pro  Gly  Arg  Ala  Tyr  Cys  Thr  Ser  Gly  Tyr  Met
               20                       25                       30
```

(2) INFORMATION FOR SEQ ID NO:34:

(i) SEQUENCE CHARACTERISTICS:
        (A) LENGTH: 32 amino acids
        (B) TYPE: amino acid
        (D) TOPOLOGY: linear (ii) MOLECULE TYPE: peptide (xi) SEQUENCE DESCRIPTION: SEQ ID NO:34:

```
Glu  Ser  Ile  Pro  Ile  Asn  Cys  Thr  Arg  Pro  Tyr  Ser  Asn  Thr  Arg  Gln
1                   5                        10                       15

Arg  Thr  Pro  Ile  Gly  Leu  Gly  Gln  Ala  Leu  Tyr  Thr  Thr  Arg  Thr  Met
               20                       25                       30
```

(2) INFORMATION FOR SEQ ID NO:35:

(i) SEQUENCE CHARACTERISTICS:
        (A) LENGTH: 32 amino acids
        (B) TYPE: amino acid
        (D) TOPOLOGY: linear (ii) MOLECULE TYPE: peptide (xi) SEQUENCE DESCRIPTION: SEQ ID NO:35:

```
Glu  Ser  Val  Val  Ile  Asn  Cys  Thr  Arg  His  Asn  Asn  Asn  Thr  Arg  Lys
1                   5                        10                       15

Ser  Ile  His  Val  Gly  Trp  Gly  Arg  Ser  Leu  Phe  Thr  Thr  Gly  Glu  Met
               20                       25                       30
```

(2) INFORMATION FOR SEQ ID NO:36:

(i) SEQUENCE CHARACTERISTICS:
        (A) LENGTH: 65 base pairs
        (B) TYPE: nucleic acid
        (C) STRANDEDNESS: both
        (D) TOPOLOGY: linear (ii) MOLECULE TYPE: DNA (genomic)

(xi) SEQUENCE DESCRIPTION: SEQ ID NO:36:

```
GATCCGTTAA CGGCTGCAGA ATCAAACAGG TCATCAACAT GTGGCAGGAA GTTGGTAAAG    60

CTATG                                                                65
```

(2) INFORMATION FOR SEQ ID NO:37:

(i) SEQUENCE CHARACTERISTICS:
        (A) LENGTH: 66 base pairs
        (B) TYPE: nucleic acid
        (C) STRANDEDNESS: both
        (D) TOPOLOGY: linear (ii) MOLECULE TYPE: DNA (genomic)

(xi) SEQUENCE DESCRIPTION: SEQ ID NO:37:

```
AGCTTAAATG ATCACAACGG ATCTGACCAG AGATCGGCGG AGCGTACATA GCTTTACCAA    60

CTTCCT                                                               66
```

( 2 ) INFORMATION FOR SEQ ID NO:38:

( i ) SEQUENCE CHARACTERISTICS:
        ( A ) LENGTH: 31 base pairs
        ( B ) TYPE: nucleic acid
        ( C ) STRANDEDNESS: both
        ( D ) TOPOLOGY: linear ( i i ) MOLECULE TYPE: DNA (genomic)

( x i ) SEQUENCE DESCRIPTION: SEQ ID NO:38:

GATCCTTTAA ACGTATCCAC ATCGGTCCGG G                31

( 2 ) INFORMATION FOR SEQ ID NO:39:

( i ) SEQUENCE CHARACTERISTICS:
        ( A ) LENGTH: 31 base pairs
        ( B ) TYPE: nucleic acid
        ( C ) STRANDEDNESS: both
        ( D ) TOPOLOGY: linear ( i i ) MOLECULE TYPE: DNA (genomic)

( x i ) SEQUENCE DESCRIPTION: SEQ ID NO:39:

TCGTGCTTTC GTTACCACCA AAAACCCGGG A                31

( 2 ) INFORMATION FOR SEQ ID NO:40:

( i ) SEQUENCE CHARACTERISTICS:
        ( A ) LENGTH: 31 base pairs
        ( B ) TYPE: nucleic acid
        ( C ) STRANDEDNESS: both
        ( D ) TOPOLOGY: linear ( i i ) MOLECULE TYPE: DNA (genomic)

( x i ) SEQUENCE DESCRIPTION: SEQ ID NO:40:

ACGACCCGGA CCGATGTGGA TACGTTTAAA G                31

( 2 ) INFORMATION FOR SEQ ID NO:41:

( i ) SEQUENCE CHARACTERISTICS:
        ( A ) LENGTH: 31 base pairs
        ( B ) TYPE: nucleic acid
        ( C ) STRANDEDNESS: both
        ( D ) TOPOLOGY: linear ( i i ) MOLECULE TYPE: DNA (genomic)

( x i ) SEQUENCE DESCRIPTION: SEQ ID NO:41:

AGCTTCCCGG GTTTTGGTG GTAACGAAAG C                31

( 2 ) INFORMATION FOR SEQ ID NO:42:

( i ) SEQUENCE CHARACTERISTICS:
        ( A ) LENGTH: 31 base pairs
        ( B ) TYPE: nucleic acid
        ( C ) STRANDEDNESS: both
        ( D ) TOPOLOGY: linear ( i i ) MOLECULE TYPE: DNA (genomic)

( x i ) SEQUENCE DESCRIPTION: SEQ ID NO:42:

GATCCATCGA TCTATCCACA TCGGTCCGGG T                31

( 2 ) INFORMATION FOR SEQ ID NO:43:

( i ) SEQUENCE CHARACTERISTICS:

(A) LENGTH: 29 base pairs
(B) TYPE: nucleic acid
(C) STRANDEDNESS: both
(D) TOPOLOGY: linear (ii) MOLECULE TYPE: DNA (genomic)

(xi) SEQUENCE DESCRIPTION: SEQ ID NO:43:

CGTGCTTTCG TTGCTACCGG TGATATCAA  29

(2) INFORMATION FOR SEQ ID NO:44:

(i) SEQUENCE CHARACTERISTICS:
(A) LENGTH: 32 base pairs
(B) TYPE: nucleic acid
(C) STRANDEDNESS: both
(D) TOPOLOGY: linear (ii) MOLECULE TYPE: DNA (genomic)

(xi) SEQUENCE DESCRIPTION: SEQ ID NO:44:

GCACGACCCG GACCGATGTG GATAGATCGA TG  32

(2) INFORMATION FOR SEQ ID NO:45:

(i) SEQUENCE CHARACTERISTICS:
(A) LENGTH: 28 base pairs
(B) TYPE: nucleic acid
(C) STRANDEDNESS: both
(D) TOPOLOGY: linear (ii) MOLECULE TYPE: DNA (genomic)

(xi) SEQUENCE DESCRIPTION: SEQ ID NO:45:

AGCTTTGATA TCACCGGTAG CAACGAAA  28

(2) INFORMATION FOR SEQ ID NO:46:

(i) SEQUENCE CHARACTERISTICS:
(A) LENGTH: 34 base pairs
(B) TYPE: nucleic acid
(C) STRANDEDNESS: both
(D) TOPOLOGY: linear (ii) MOLECULE TYPE: DNA (genomic)

(xi) SEQUENCE DESCRIPTION: SEQ ID NO:46:

GATCCTTTAA ATCTATCCGT ATCACCAAAG GTCC  34

(2) INFORMATION FOR SEQ ID NO:47:

(i) SEQUENCE CHARACTERISTICS:
(A) LENGTH: 34 base pairs
(B) TYPE: nucleic acid
(C) STRANDEDNESS: both
(D) TOPOLOGY: linear (ii) MOLECULE TYPE: DNA (genomic)

(xi) SEQUENCE DESCRIPTION: SEQ ID NO:47:

GGGTCGTGTT ATCGTTGCTA CCGGTCAAGA TCTA  34

(2) INFORMATION FOR SEQ ID NO:48:

(i) SEQUENCE CHARACTERISTICS:
(A) LENGTH: 34 base pairs
(B) TYPE: nucleic acid
(C) STRANDEDNESS: both
(D) TOPOLOGY: linear (ii) MOLECULE TYPE: DNA (genomic)

(xi) SEQUENCE DESCRIPTION: SEQ ID NO:48:

ACCCGGACCT TTGGTGATAC GGATAGATTT AAAG 34

(2) INFORMATION FOR SEQ ID NO:49:

(i) SEQUENCE CHARACTERISTICS:
        (A) LENGTH: 34 base pairs
        (B) TYPE: nucleic acid
        (C) STRANDEDNESS: both
        (D) TOPOLOGY: linear (ii) MOLECULE TYPE: DNA (genomic)

(xi) SEQUENCE DESCRIPTION: SEQ ID NO:49:

AGCTTAGATC TTGACCGGTA GCAACGATAA CACG 34

(2) INFORMATION FOR SEQ ID NO:50:

(i) SEQUENCE CHARACTERISTICS:
        (A) LENGTH: 62 base pairs
        (B) TYPE: nucleic acid
        (C) STRANDEDNESS: both
        (D) TOPOLOGY: linear (ii) MOLECULE TYPE: DNA (genomic)

(xi) SEQUENCE DESCRIPTION: SEQ ID NO:50:

GATCCTTTAA ATCTATCCGT ATCCAGCGTG GTCCGGGTCG TGCTTTCGTT ACCATCGGTA 60

AA 62

(2) INFORMATION FOR SEQ ID NO:51:

(i) SEQUENCE CHARACTERISTICS:
        (A) LENGTH: 62 base pairs
        (B) TYPE: nucleic acid
        (C) STRANDEDNESS: both
        (D) TOPOLOGY: linear (ii) MOLECULE TYPE: DNA (genomic)

(xi) SEQUENCE DESCRIPTION: SEQ ID NO:51:

AGCTTTTACC GATGGTAACG AAAGCACGAC CCGGACCACG CTGGATACGG ATAGATTTAA 60

AG 62

(2) INFORMATION FOR SEQ ID NO:52:

(i) SEQUENCE CHARACTERISTICS:
        (A) LENGTH: 31 base pairs
        (B) TYPE: nucleic acid
        (C) STRANDEDNESS: both
        (D) TOPOLOGY: linear (ii) MOLECULE TYPE: DNA (genomic)

(xi) SEQUENCE DESCRIPTION: SEQ ID NO:52:

GATCCATCGA TCTCTGTCTA TCGGTCCGGG T 31

(2) INFORMATION FOR SEQ ID NO:53:

(i) SEQUENCE CHARACTERISTICS:
        (A) LENGTH: 27 base pairs
        (B) TYPE: nucleic acid
        (C) STRANDEDNESS: both
        (D) TOPOLOGY: linear (ii) MOLECULE TYPE: DNA (genomic)

( x i ) SEQUENCE DESCRIPTION: SEQ ID NO:53:

CGTGCTTTCC GTACCCGTGA AGATCTA                                          27

( 2 ) INFORMATION FOR SEQ ID NO:54:

( i ) SEQUENCE CHARACTERISTICS:
        ( A ) LENGTH: 32 base pairs
        ( B ) TYPE: nucleic acid
        ( C ) STRANDEDNESS: both
        ( D ) TOPOLOGY: linear ( i i ) MOLECULE TYPE: DNA (genomic)

( x i ) SEQUENCE DESCRIPTION: SEQ ID NO:54:

GCACGACCCG GACCGATAGA CAGAGATCGA TG                                    32

( 2 ) INFORMATION FOR SEQ ID NO:55:

( i ) SEQUENCE CHARACTERISTICS:
        ( A ) LENGTH: 26 base pairs
        ( B ) TYPE: nucleic acid
        ( C ) STRANDEDNESS: both
        ( D ) TOPOLOGY: linear ( i i ) MOLECULE TYPE: DNA (genomic)

( x i ) SEQUENCE DESCRIPTION: SEQ ID NO:55:

AGCTTAGATC TTCACGGGTA CGGAAA                                           26

( 2 ) INFORMATION FOR SEQ ID NO:56:

( i ) SEQUENCE CHARACTERISTICS:
        ( A ) LENGTH: 28 base pairs
        ( B ) TYPE: nucleic acid
        ( C ) STRANDEDNESS: both
        ( D ) TOPOLOGY: linear ( i i ) MOLECULE TYPE: DNA (genomic)

( x i ) SEQUENCE DESCRIPTION: SEQ ID NO:56:

AGACCCGGAC CCGGAAGAAT AGTGATAA                                         28

( 2 ) INFORMATION FOR SEQ ID NO:57:

( i ) SEQUENCE CHARACTERISTICS:
        ( A ) LENGTH: 32 base pairs
        ( B ) TYPE: nucleic acid
        ( C ) STRANDEDNESS: both
        ( D ) TOPOLOGY: linear ( i i ) MOLECULE TYPE: DNA (genomic)

( x i ) SEQUENCE DESCRIPTION: SEQ ID NO:57:

AGCTTTATCA CTATTCTTCC GGGTCCGGGT CT                                    32

( 2 ) INFORMATION FOR SEQ ID NO:58:

( i ) SEQUENCE CHARACTERISTICS:
        ( A ) LENGTH: 18 base pairs
        ( B ) TYPE: nucleic acid
        ( C ) STRANDEDNESS: both
        ( D ) TOPOLOGY: linear ( i i ) MOLECULE TYPE: DNA (genomic)

( x i ) SEQUENCE DESCRIPTION: SEQ ID NO:58:

CCGCCAGATC CGGATCCG                                                    18

( 2 ) INFORMATION FOR SEQ ID NO:59:

( i ) SEQUENCE CHARACTERISTICS:
        ( A ) LENGTH: 14 base pairs
        ( B ) TYPE: nucleic acid
        ( C ) STRANDEDNESS: both
        ( D ) TOPOLOGY: linear ( i i ) MOLECULE TYPE: DNA (genomic)

( x i ) SEQUENCE DESCRIPTION: SEQ ID NO:59:

CCGCCGGCAA GCTT    14

( 2 ) INFORMATION FOR SEQ ID NO:60:

( i ) SEQUENCE CHARACTERISTICS:
        ( A ) LENGTH: 13 base pairs
        ( B ) TYPE: nucleic acid
        ( C ) STRANDEDNESS: both
        ( D ) TOPOLOGY: linear ( i i ) MOLECULE TYPE: DNA (genomic)

( x i ) SEQUENCE DESCRIPTION: SEQ ID NO:60:

AGATCCGGAT CCG    13

( 2 ) INFORMATION FOR SEQ ID NO:61:

( i ) SEQUENCE CHARACTERISTICS:
        ( A ) LENGTH: 27 base pairs
        ( B ) TYPE: nucleic acid
        ( C ) STRANDEDNESS: both
        ( D ) TOPOLOGY: linear ( i i ) MOLECULE TYPE: DNA (genomic)

( x i ) SEQUENCE DESCRIPTION: SEQ ID NO:61:

AACGGCTGCA GAATCAAACA GGTCATC    27

( 2 ) INFORMATION FOR SEQ ID NO:62:

( i ) SEQUENCE CHARACTERISTICS:
        ( A ) LENGTH: 30 base pairs
        ( B ) TYPE: nucleic acid
        ( C ) STRANDEDNESS: both
        ( D ) TOPOLOGY: linear ( i i ) MOLECULE TYPE: DNA (genomic)

( x i ) SEQUENCE DESCRIPTION: SEQ ID NO:62:

AAGCTTGCCG GCGCATCACA ACGGATCTGA    30

( 2 ) INFORMATION FOR SEQ ID NO:63:

( i ) SEQUENCE CHARACTERISTICS:
        ( A ) LENGTH: 29 base pairs
        ( B ) TYPE: nucleic acid
        ( C ) STRANDEDNESS: both
        ( D ) TOPOLOGY: linear ( i i ) MOLECULE TYPE: DNA (genomic)

( x i ) SEQUENCE DESCRIPTION: SEQ ID NO:63:

AGATCCGGAT CCGAAACGTA TCCACATCG    29

( 2 ) INFORMATION FOR SEQ ID NO:64:

( i ) SEQUENCE CHARACTERISTICS:
        ( A ) LENGTH: 29 base pairs ( B ) TYPE: nucleic acid
        ( C ) STRANDEDNESS: both
        ( D ) TOPOLOGY: linear ( i i ) MOLECULE TYPE: DNA (genomic)

( x i ) SEQUENCE DESCRIPTION: SEQ ID NO:64:

AAGCTTGCCG GCGGGTTTTT GGTGGTAAC 29

( 2 ) INFORMATION FOR SEQ ID NO:65:

( i ) SEQUENCE CHARACTERISTICS:
        ( A ) LENGTH: 28 base pairs
        ( B ) TYPE: nucleic acid
        ( C ) STRANDEDNESS: both
        ( D ) TOPOLOGY: linear ( i i ) MOLECULE TYPE: DNA (genomic)

( x i ) SEQUENCE DESCRIPTION: SEQ ID NO:65:

AGATCCGGAT CCGCGATCTA TCCACATC 28

( 2 ) INFORMATION FOR SEQ ID NO:66:

( i ) SEQUENCE CHARACTERISTICS:
        ( A ) LENGTH: 30 base pairs
        ( B ) TYPE: nucleic acid
        ( C ) STRANDEDNESS: both
        ( D ) TOPOLOGY: linear ( i i ) MOLECULE TYPE: DNA (genomic)

( x i ) SEQUENCE DESCRIPTION: SEQ ID NO:66:

AAGCTTGCCG GCGGATCACC GGTAGCAACG 30

( 2 ) INFORMATION FOR SEQ ID NO:67:

( i ) SEQUENCE CHARACTERISTICS:
        ( A ) LENGTH: 29 base pairs
        ( B ) TYPE: nucleic acid
        ( C ) STRANDEDNESS: both
        ( D ) TOPOLOGY: linear ( i i ) MOLECULE TYPE: DNA (genomic)

( x i ) SEQUENCE DESCRIPTION: SEQ ID NO:67:

AGATCCGGAT CCGAAATCTA TCCGTATCA 29

( 2 ) INFORMATION FOR SEQ ID NO:68:

( i ) SEQUENCE CHARACTERISTICS:
        ( A ) LENGTH: 28 base pairs
        ( B ) TYPE: nucleic acid
        ( C ) STRANDEDNESS: both
        ( D ) TOPOLOGY: linear ( i i ) MOLECULE TYPE: DNA (genomic)

( x i ) SEQUENCE DESCRIPTION: SEQ ID NO:68:

AAGCTTGCCG GCGGTTGACC GGTAGCAA 28

( 2 ) INFORMATION FOR SEQ ID NO:69:

( i ) SEQUENCE CHARACTERISTICS:
        ( A ) LENGTH: 28 base pairs
        ( B ) TYPE: nucleic acid
        ( C ) STRANDEDNESS: both
        ( D ) TOPOLOGY: linear ( i i ) MOLECULE TYPE: DNA (genomic)

( x i ) SEQUENCE DESCRIPTION: SEQ ID NO:69:

AGATCCGGAT CCGAAATCTA TCCGTATC                    28

( 2 ) INFORMATION FOR SEQ ID NO:70:

( i ) SEQUENCE CHARACTERISTICS:
        ( A ) LENGTH: 30 base pairs
        ( B ) TYPE: nucleic acid
        ( C ) STRANDEDNESS: both
        ( D ) TOPOLOGY: linear ( i i ) MOLECULE TYPE: DNA (genomic)

( x i ) SEQUENCE DESCRIPTION: SEQ ID NO:70:

AAGCTTGCCG GCGGTTTACC GATGGTAACG                  30

( 2 ) INFORMATION FOR SEQ ID NO:71:

( i ) SEQUENCE CHARACTERISTICS:
        ( A ) LENGTH: 29 base pairs
        ( B ) TYPE: nucleic acid
        ( C ) STRANDEDNESS: both
        ( D ) TOPOLOGY: linear ( i i ) MOLECULE TYPE: DNA (genomic)

( x i ) SEQUENCE DESCRIPTION: SEQ ID NO:71:

AGATCCGGAT CCGCGATCTC TGTCTATCG                   29

( 2 ) INFORMATION FOR SEQ ID NO:72:

( i ) SEQUENCE CHARACTERISTICS:
        ( A ) LENGTH: 28 base pairs
        ( B ) TYPE: nucleic acid
        ( C ) STRANDEDNESS: both
        ( D ) TOPOLOGY: linear ( i i ) MOLECULE TYPE: DNA (genomic)

( x i ) SEQUENCE DESCRIPTION: SEQ ID NO:72:

AAGCTTGCCG GCGGTTCACG GGTACGGA                    28

( 2 ) INFORMATION FOR SEQ ID NO:73:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:73:

Pro Pro Asp Pro Asp Pro
1               5